United States Patent
Tsuchiya et al.

(10) Patent No.: US 8,983,113 B2
(45) Date of Patent: *Mar. 17, 2015

(54) DEFECT ESTIMATION DEVICE AND METHOD AND INSPECTION SYSTEM AND METHOD

(71) Applicant: NuFlare Technology, Inc., Numazu-shi (JP)

(72) Inventors: Hideo Tsuchiya, Tokyo (JP); Takayuki Abe, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 280 days.

This patent is subject to a terminal disclaimer.

(21) Appl. No.: 13/705,663

(22) Filed: Dec. 5, 2012

(65) Prior Publication Data

US 2013/0093878 A1 Apr. 18, 2013

Related U.S. Application Data

(62) Division of application No. 13/017,641, filed on Jan. 31, 2011, now Pat. No. 8,737,676.

(30) Foreign Application Priority Data

Feb. 1, 2010 (JP) ................................. 2010-020584
Mar. 23, 2010 (JP) ................................. 2010-066559

(51) Int. Cl.
G06K 9/00 (2006.01)
G06T 7/00 (2006.01)

(52) U.S. Cl.
CPC .............. G06T 7/001 (2013.01); G06T 7/0002 (2013.01)
USPC ........... 382/100; 382/149; 382/144; 382/154; 382/248; 382/283

(58) Field of Classification Search
CPC .............................. G06T 7/0002; G06T 7/001
USPC .................. 382/100, 149, 144, 154, 248, 283
See application file for complete search history.

(56) References Cited

U.S. PATENT DOCUMENTS 6,578,188 B1 6/2003 Pang et al.
6,757,645 B2 6/2004 Chang et al.
(Continued)

FOREIGN PATENT DOCUMENTS

JP 2001-66759 A 3/2001
JP 2001-516898 10/2001
(Continued)

OTHER PUBLICATIONS

Office Action issued Aug. 5, 2014 in Japanese Patent Application No. 2011-017294 with English language translation.
(Continued)

*Primary Examiner* — Mike Rahmjoo
(74) *Attorney, Agent, or Firm* — Oblon, McClelland, Maier & Neustadt, L.L.P.

(57) ABSTRACT

Acquired mask data of a defect portion is sent to a simulated repair circuit 300 to be simulated. The simulation of the acquired mask data 204 is returned to the mask inspection results 205 and thereafter sent to a wafer transfer simulator 400 along with a reference image at the corresponding portion. A wafer transfer image estimated by the wafer transfer simulator 400 is sent to a comparing circuit 301. When it is determined that there is a defect in the comparing circuit 301, the coordinates and the wafer transfer image which is a basis for the defect determination are stored as transfer image inspection results 206. The mask inspection results 205 and the transfer image inspection result 206 are then sent to the review device 500.

10 Claims, 23 Drawing Sheets

(56) References Cited

U.S. PATENT DOCUMENTS

| | | | |
|---|---|---|---|
| 6,873,720 B2 * | 3/2005 | Cai et al. | 382/149 |
| 7,003,758 B2 | 2/2006 | Ye et al. | |
| 7,043,071 B2 | 5/2006 | Qian et al. | |
| 7,221,788 B2 * | 5/2007 | Schulze et al. | 382/144 |
| 7,665,060 B2 | 2/2010 | Luc-Pat et al. | |
| 7,872,745 B2 | 1/2011 | Abe et al. | |
| 7,973,918 B2 | 7/2011 | Tsuchiya et al. | |
| 8,031,932 B2 | 10/2011 | Tsuchiya et al. | |
| 8,078,012 B2 | 12/2011 | Abe et al. | |
| 8,355,044 B2 | 1/2013 | Tsuchiya et al. | |
| 2004/0172611 A1 | 9/2004 | Pang | |
| 2011/0044528 A1 | 2/2011 | Tsuchiya et al. | |
| 2011/0044529 A1 | 2/2011 | Tsuchiya et al. | |
| 2011/0176719 A1 | 7/2011 | Inoue et al. | |
| 2012/0140060 A1 | 6/2012 | Tsuchiya et al. | |
| 2013/0044205 A1 | 2/2013 | Matsumoto et al. | |

FOREIGN PATENT DOCUMENTS

| | | |
|---|---|---|
| JP | 2001-516898 A | 10/2001 |
| JP | 2008-112178 | 5/2008 |
| JP | 2009-105430 | 5/2009 |
| WO | WO 99/14706 A2 | 3/1999 |

OTHER PUBLICATIONS

Carl Hess, et al., "A Novel Approach: High Resolution Inspection with Wafer Plane Defect Detection", (KLA-Tencor Corporation), Proc. of SPIE vol. 7028, 70281F, 2008, pp. 1-11.

Dan Rost, et al., "Qualification of Aerial Image 193nm Inspection Tool for All Masks and All Process Steps", (MP-Mask Technology Center), Proc. of SPIE vol. 7028, 70282Q, 2008, pp. 1-12.

H.H. Hopkins, "On the Diffraction Theory of Optical Images", In Proc. Royal Soc. Series A., vol. 217, No. 1131, 1953, pp. 408-432.

N. Cobb, et al., "Experimental Results on Optical Proximity Correction with Variable Threshold Resist Model", Proc. SPIE 3051, 1997, pp. 458-468.

Morimi Osawa, et al., "Correction for Local Flare Effects Approximated with Double Gaussian Profile in ArF Lithography", J. Vac. Sci. Technol. B 21(6), Nov./Dec. 2003, pp. 2806-2809.

Nicolas Bailey Cobb, "Fast Optical and Process Proximity Correction Algorithms for Integrated Circuit Manufacturing", Engineering: Electrical Engineering and Computer Science, Spring 1998, 139 pages.

* cited by examiner

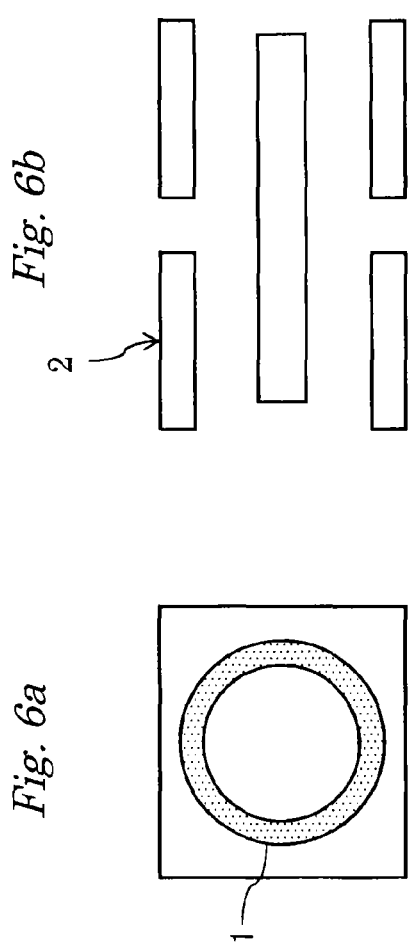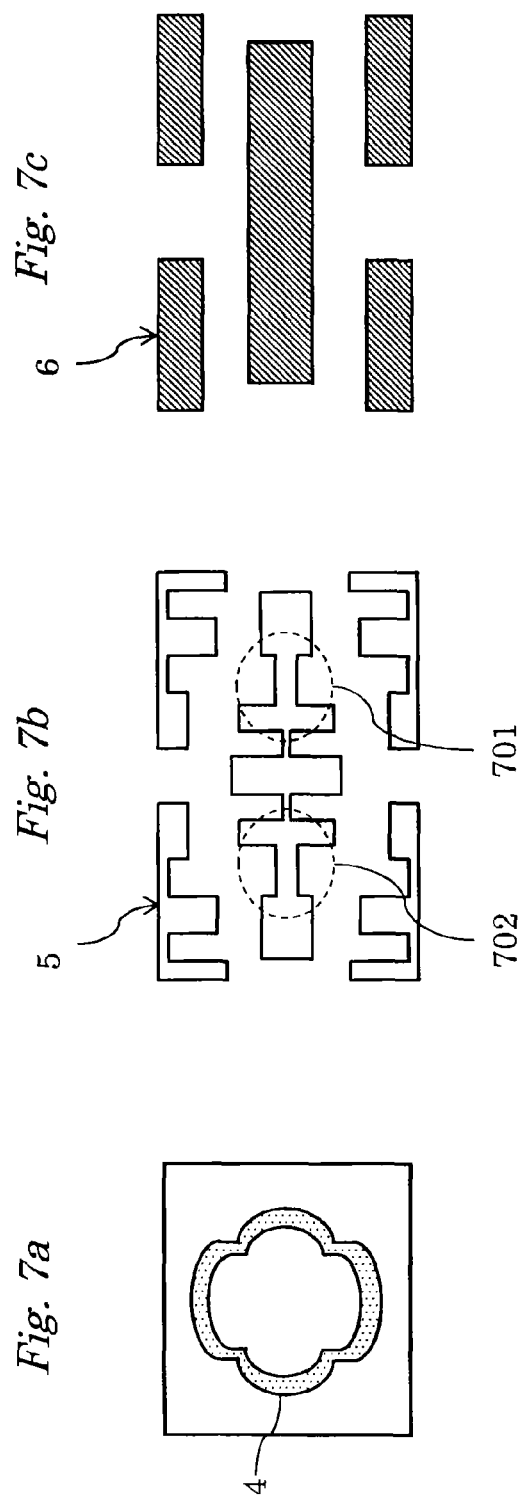

DEFECT ESTIMATION DEVICE AND METHOD AND INSPECTION SYSTEM AND METHOD

CROSS-REFERENCE TO RELATED APPLICATIONS

This application is a Division of and claims the benefit of priority under 35 U.S.C. §120 from U.S. Ser. No. 13/017,641, filed Jan. 31, 2011, and claims the benefit of priority under 35 U.S.C. §119 from Japanese Patent Applications 2010-020584 filed Feb. 1, 2010 and 2010-066559 filed Mar. 23, 2010, the entire contents of each of which are incorporated herein by reference.

BACKGROUND OF THE INVENTION

1. Field of the Invention

The present invention relates to a defect estimation device and method used to estimate defects of a pattern formed on an object to be inspected such as a mask, and an inspection system and inspection method used to detect defects of a pattern formed on an object to be inspected.

2. Background Art

In recent years, as the levels of integration and capacity of large scale integrated circuits (LSIs) have increased, there has been a need to continue to reduce the width of the circuit patterns of semiconductor devices. Semiconductor devices are manufactured by a reduced projection exposure apparatus called a "stepper" using original artwork patterns with a circuit pattern formed thereon, these are called masks or reticles (hereinafter referred to collectively as masks). Specifically, a pattern on a mask is transferred to the wafer by exposure to light, thereby forming circuits on to a wafer. Masks used to transfer such fine circuit patterns to the wafer are manufactured by electron beam writing apparatuses, which can write micropatterns. Further, effort has been made to develop a laser beam writing apparatus, which uses a laser beam for writing. It should be noted that electron beam apparatuses are also used to directly write a circuit pattern on a wafer.

Incidentally, since the cost to manufacture LSIs is very high, an increase in yield is required to make the manufacturing economically feasible. Meanwhile, recent representative logic devices require a pattern having a line width of several ten nano-meters. Major factors that reduce the yield include a mask containing a pattern defect and a variation in conditions of the exposure transfer. In the prior art, with the miniaturization of an LSI pattern dimension to be formed on a semiconductor wafer, mask dimensional accuracy has been improved, by the variation margin of process terms and conditions having been absorbed. Therefore, in the mask inspection, the dimension of the pattern defect is miniaturized, and a positional error of an extremely small pattern is required to be inspected. Therefore, high inspection accuracy is required of inspection systems for detecting defects of masks used in LSI manufacture.

One of the factors that allow miniaturization of a mask pattern is the application of Resolution Enhancement Technology (herein after referred to as RET). In the RET technique, an auxiliary pattern referred to as an assist pattern is disposed on the side of a main pattern, whereby the formability of the main pattern is improved. Although the auxiliary pattern is not part of a transfer image, light energy entering a region of the main pattern is secured by the provision of the auxiliary pattern. In a mask inspection device, such a defect of the assist pattern can also be detected.

There are two known mask defect detecting methods: the die-to-die inspection method and the die-to-database inspection method. The die-to-die inspection method is used when the mask to be inspected has thereon a plurality of identical chip patterns, or a plurality of chip patterns each including an identical pattern segment. In this method, these identical chip patterns or identical pattern segments, which are to be printed to the wafer, are compared to each other. This method permits accurate inspection using a relatively simple system configuration, since patterns on the same mask are directly compared to each other. However, this method cannot detect a defect common to both compared patterns. In the die-to-database inspection method, on the other hand, an actual pattern on a mask is compared to reference data generated from the design pattern data that was used to manufacture the mask. Thus, this method allows exact comparison of the pattern with the design pattern data, although the required system size is large since the method requires a processing system for generating a reference image. There is no choice but to use this inspection method when the mask to be inspected has only one chip pattern to be transferred to the wafer.

In die-to-die inspection, light is emitted from a light source, and the mask to be inspected is irradiated with this light through an optical system. The mask is mounted on a table, and this table is moved so that the emitted beam of light scans the surface of the mask. Light transmitted through or reflected from the mask reaches an image sensor, thereby forming an image thereon. The optical image thus formed on the image sensor is sent to a comparing unit as measurement data. The comparing unit compares the measurement data with reference data in accordance with an appropriate algorithm, and if they are not identical, the mask is determined to have a defect (see Patent Document 1).

In the prior art inspection device, when it is determined that there is a defect, the optical image used as a basis for the determination and the corresponding reference image are stored in the inspection device along with the coordinates of these images. When the inspection of one mask is completed, an operator visually confirms a pattern at a defect portion utilizing an optical observation system in the inspection device. Then, the necessity of repair is determined. After a defect to be repaired is discovered the mask and the information required for the repair are sent to a repair device. The information required for the repair is a cut-out portion of pattern data for use in the recognition of coordinates in the mask, discrimination between extrusion and intrusion defects, discrimination whether to remove a light-shielding film or deposit a pattern at a portion to be repaired by the repair device.

As described above, in the prior art inspection device, a mask pattern image obtained by imaging an optical image by an image sensor is determined to be correct. However, with the recent miniaturization of a device pattern on a mask, it is difficult to distinguish a difference between a shape defect of a pattern and a potentially existing shape error of a pattern. Incidentally, defects associated with micropatterns include not only shape defects typified by pattern edge roughness, but also pattern linewidth errors and pattern displacement errors, which are becoming more and more significant due to the miniaturization of device patterns. Therefore, there has been a strong need to accurately control the dimensions of patterns, thus increasing the difficulty of manufacturing masks. As a result, there has been a loss in the yield of masks that meet the required specifications, thereby raising mask manufacturing cost. Further, the required accuracy of a linewidth or pattern of a mask increases, whereby determination as to whether or not there is a defect is difficult if the only comparison is between generated reference data based on design pattern data and a pattern image taken by an inspection device.

In order to address this problem, a defect evaluating method has been proposed which uses a simulation. This method simulates the image which would be printed from the mask to a wafer by the photolithography apparatus and determines whether or not the pattern on the mask is defective by inspecting the simulated image. Non-Patent Document 1 shows a method of capturing an inspected mask image by a CCD (Charge Coupled Device), using a high-resolution optical system and a method of obtaining a wafer aerial image by using a low-resolution optical system (see, FIG. 1). In the former method, the mask image of the inspected pattern and the reference pattern is acquired by the high-resolution optical system. A wafer transfer image is estimated from the mask image through the process of FIG. 2. Thereafter, the wafer transfer images are compared with each other and defect determination is performed. Meanwhile, in the latter method, the wafer transfer image is directly collected by an optical wafer transfer device. In these methods, an image to be transferred onto a wafer is predicted, and the defect determination is performed based on the image. The latter method is also described in Non-Patent Document 2 (see, FIG. 3 and the bottom of page 3).

When a plurality of fractures and taper shaped defects occur in an assist pattern corresponding to a certain part of the main pattern on a mask, the shape of the main pattern in an estimated wafer transfer image should be in such a state that a dimensional error such as constriction of the line width occurs. That is to say, according to a determination method based on a transfer image, it can be predicted that the shape defect of a mask makes the transfer image incorrect. However, in this case, there is a problem that it cannot be indicated which of the defect portions in the assist pattern, that is, which of a plurality of fracture portions causes the constriction of the line width in the main pattern, or which combination of the plurality of fracture portions causes the constriction of the line width in the main pattern.

Patent Document 2 discloses a method for simulating a lithographic design comprised of a number of polygons arranged in a predetermined configuration. Specifically, referring to FIG. 4 of this publication, an aerial image is generated using a bitmap image available from the polygon design database (box 126), and resist modeling or simulation is performed using this aerial image (box 128). FIG. 7 shows a technique of estimating a wafer pattern aerial image by simulation of an image from a mask inspection device. This technique indicates whether a wafer aerial image or a wafer image, obtained through a wafer generation process such as reaction of photoresist by light exposure, is correct.

Further, Patent Document 3 states as follows: "In any mask inspection system, the important decision to make is whether a given defect will 'print' on the underlying photoresist in a lithography process under specified conditions. If a mask defect does not print or have other effect on the lithography process, then the mask with the defect can still be used to provide acceptable lithography results. Therefore, one can avoid the expense in time and cost of repairing and/or replacing masks whose defects do not print."

Patent Document 3 discloses a method of acquiring a defect area image including an image of a portion of a mask and generating a simulated image. This simulated image includes a simulation of an image which would be printed on the wafer.

As described above, according to the prior art inspection device, an estimated transfer image that would be transferred to the wafer including defects acquired by the inspection device can be generated. However, in the prior art there is no inspection device which can indicate the level of influence that a defect will have on the wafer. Furthermore, there is no inspection device that can determine whether the repair of a specific pattern error or repair of a combination of pattern errors in the wafer transfer image will result in an acceptable transfer image to the wafer. For example, when a pattern is formed on the wafer using an exposure light source having a directivity in irradiation intensity, a irradiation direction and a mask pattern that have been optimized, a minute pattern can be transferred onto the wafer in combination with the exposure light. Estimation is then required to determine which portion of the wafer transfer image is affected by the mask shape defect using accurate simulation including a light source.

[Patent Document 1] Japanese laid-open Patent publication No. 2008-112178

[Patent Document 2] Japanese laid-open Patent publication No. 2009-105430

[Patent Document 3] Published Japanese translation of PCT application No. 2001-516898

[Non-Patent Document 1] Carl Hess et al. (KLA-Tencor Corporation), A Novel Approach: High Resolution Inspection with a Wafer Plane Defect Detection. Prof of SPIE Vol. 7028, 70281F

[Non-Patent Document 2] Dan Ros et al. (MP-Mask Technology Center) Qualification of Aerial Image 193 nm Inspection Tool for All Masks and All Process Steps, Proc of SPIE Vol. 7028, 70282Q (2008)

[Non-Patent Document 3] (H. H. Hopkins, On the di_reaction theory of optical images, In Proc. Royal Soc. Series A., volume 217 No. 1131, pages 408-432, 1953).

[Non-Patent Document 4] (N. B. Cobb, A. Zakhor, M. Reihani, F. Jahansooz, and V. N. Raghavan: Proc. SPIE 3051 (1997) 458).

[Non-Patent Document 5] (M. Osawa, T. Yao, H. Aoyama, K. Ogino, H. Hoshino, Y. Machida, S. Asai, and H. Arimoto, J. Vac. Sci. Technol. B21 (2003) 2806).

[Non-Patent Document 6] N. B Cobb, (Fast Optical and Process Proximity Correction Algorithms for Integrated Circuit Manufacturing) A dissertation submitted in partial satisfaction of the requirements for the degree of Doctor Of Philosophy in Engineering: Electrical Engineering and Computer Science in the Graduate Division of the University of California in Berkeley, Spring 1988 can be referred to.

The present invention has been conceived in view of the above problem. Therefore, an object of this invention is to provide a defect estimation device and a defect estimation method, which can estimate a defect or a plurality of defects on a mask, the influence of the defect on a wafer, and the degree of improvement by repair.

Further, an object of this invention is to provide an inspection device which estimates a defect on a mask, the influence of the defect on a wafer and the degree of improvement by repair, thereby indicating the level of influence of the mask defect itself on the wafer and the portion of the pattern on the mask to be repaired for eliminating a detected defect.

Furthermore, another object of this invention is to provide an inspection device and an inspection method, which can facilitate a defect determination processing for a mask and can perform defect determination processing and estimate a defect or a plurality of defects on a mask and the resultant influence on a wafer image.

Other challenges and advantages of the present invention are apparent from the following description.

SUMMARY OF THE INVENTION

The present invention relates to a Defect Estimation Device and Method and an Inspection System and Method. In the first aspect, a defect estimation device comprising: an estimation part which obtains an optical image of a pattern formed on a mask and a reference image and then estimates from these images each pattern image that would be transferred to a substrate; a comparison part which compares the pattern images with each other and when a difference exceeds at least one of the threshold values, determines that there is a defect; and a simulated repair part which simulates a repair to the optical image at a portion determined as defective by the comparison, wherein the simulated optical image is sent to the estimation part.

In another aspect of this invention, a defect estimation device comprising: a first estimation part which obtains an optical image of a pattern formed on a mask and a reference image and estimates, from these images, each first pattern image of the patterns transferred to a substrate by a lithography process; a first comparison part which compares the first pattern images with each other and, when a difference exceeds at least one of the threshold values, determines that there is a defect; a simulated repair part which simulates a repair to the optical image at a portion determined as defective by the comparison; and a second estimation part which estimates each second pattern image of the patterns, transferred onto the substrate, from the reference image and the simulated optical image, wherein in the second pattern image, the lithography process is more advanced than that in the first pattern image.

In another aspect of this invention, a defect estimation method comprising: obtaining an optical image of a pattern formed on a mask and a reference image, estimating from these images, each first pattern image of the patterns transferred to a substrate, and comparing the first pattern images with each other; simulating a repair to the optical image at a portion determined as defective by the comparison; and estimating, after the simulated repair, each second pattern image from the reference image and the simulated optical image.

In another aspect of this invention, an inspection device, which irradiates light to a mask formed with a pattern, forming an image of the mask on an image sensor through an optical system, and determines the presence of a defect, comprising: an optical image acquisition part which obtains an optical image of the mask from the image sensor; an estimation part which estimates each pattern image of the patterns, transferred to a substrate, from a reference image as a reference of the determination and the optical image; a comparison part which compares the pattern images with each other and, when a difference exceeds at least one of the threshold values, determines that there is a defect; and a simulated repair part which simulates a repair to the optical image at a portion determined as a defective by the comparison, wherein the simulated optical image is sent to the estimation part.

In another aspect of this invention, an inspection device, which irradiates light to a mask formed with a pattern, forming an image of the mask on an image sensor through an optical system, and determines the presence of a defect, comprising:
an optical image acquisition part which obtains an optical image of the mask from the image sensor; a first estimation part which estimates, from a reference image as a reference of the determination and the optical image, each first pattern image of the patterns transferred to a substrate by a lithography process; a first comparison part which compares the first pattern images with each other and, when a difference exceeds at least one of the threshold values, determines that there is a defect; a simulated repair part which simulates a repair to the optical image at a portion determined as defective by the comparison; and a second estimation part which estimates each second pattern image of the patterns, transferred onto the substrate, from the reference image and the simulated optical image, wherein in the second pattern image, the lithography process is more advanced than that in the first pattern image.

In another aspect of this invention, an inspection device, which irradiates light to a sample formed with a pattern, forming an image of the sample on an image sensor through an optical system, and determines the presence of a defect, comprising: an optical image acquisition part which obtains an optical image of the sample from the image sensor; a first comparison part which compares the optical image with a reference image as a reference of the determination and, when a difference exceeds at least one of the threshold values, determines that there is a defect; a transfer image estimation part which estimates by simulation an optical image obtained when each pattern of an optical image on the sample and the reference image is transferred by a transfer device; and a second comparison part which compares each of the transfer images and when a difference exceeds at least one of the threshold values, determines that there is a defect.

In another aspect of this invention, an inspection device, which irradiates light to a sample formed with a pattern, forming an image of the sample on an image sensor through an optical system, and determines the presence of a defect, comprising: an optical image acquisition part which obtains an optical image of the sample from the image sensor; a first comparison part which compares the optical image with a reference image as a reference of the determination and when a difference exceeds at least one of the threshold values, determines that there is a defect; a simulated repair part which obtains the optical image determined as a defect by the first comparison part and simulates a repair to the defect; a transfer image estimation part which estimates a transfer image of the optical image simulated by the simulated repair part and a transfer image of the reference image by simulation; and a second comparison part which compares each of the transfer images and when a difference exceeds at least one of the threshold values, determines that there is a defect.

In another aspect of this invention, an inspection method, which irradiates light to a sample formed with a pattern, forming an image of the sample on an image sensor through an optical system, and determines the presence of a defect, comprising the steps of: obtaining an optical image of the sample from the image sensor; comparing the optical image with a reference image as a reference of the determination and, when a difference exceeds at least one of the threshold values, determining that there is a defect; estimating a transfer image of the optical image and a transfer image of the reference image by simulation; comparing the transfer image of the optical image and the transfer image of the reference image and, when a difference exceeds at least one of the threshold values, determining that there is a defect and reviewing the optical image, the reference image, and each of the transfer images and determining necessity of repair to be applied to the defect.

In another aspect of this invention, an inspection method comprising the steps of: illuminating light to a sample formed with a pattern, forming an image of the sample on an image sensor through an optical system, obtaining an optical image of the sample from the image sensor, and comparing the obtained optical image with a reference image and when a difference exceeds at least one of the threshold values, determining that there is a defect, reviewing the optical image including the defect and the reference image corresponding to the optical image and determining necessity of repair be applied to the defect, determining whether or not each transfer image of the optical image and the reference image is required to be estimated, when each of the transfer images is required to be estimated, estimating and comparing each of the transfer images, when a difference exceeds at least one of the threshold values, determining that there is a defect, reviewing each of the transfer images, and determining the necessity of the repair applied to the defect and when each of the transfer images is not required to be estimated, reviewing an optical image including another defect and a reference image corresponding to the optical image, and determining the necessity of the repair applied to another defect. Wherein, when each of the transfer images is required to be estimated, a transfer image of the simulated optical image is estimated.

BRIEF DESCRIPTION OF THE DRAWINGS

FIG. 6a is an example schematically showing the shape of a surface irradiated with the exposure light source according to Embodiment 1.

FIG. 6b is a mask having a pattern shape to be used with the above light source according to Embodiment 1.

FIG. 6c is a transfer image resulting from the above light source and mask pattern according to Embodiment 1.

FIG. 7a is an example schematically showing the shape of a surface irradiated with the exposure light source according to Embodiment 1.

FIG. 7b is a mask having a pattern shape to be used with the above light source according to Embodiment 1.

FIG. 7c is a transfer image resulting from the above light source and mask pattern according to Embodiment 1.

DETAILED DESCRIPTION OF THE EMBODIMENTS

Embodiment 1

Figure 1:
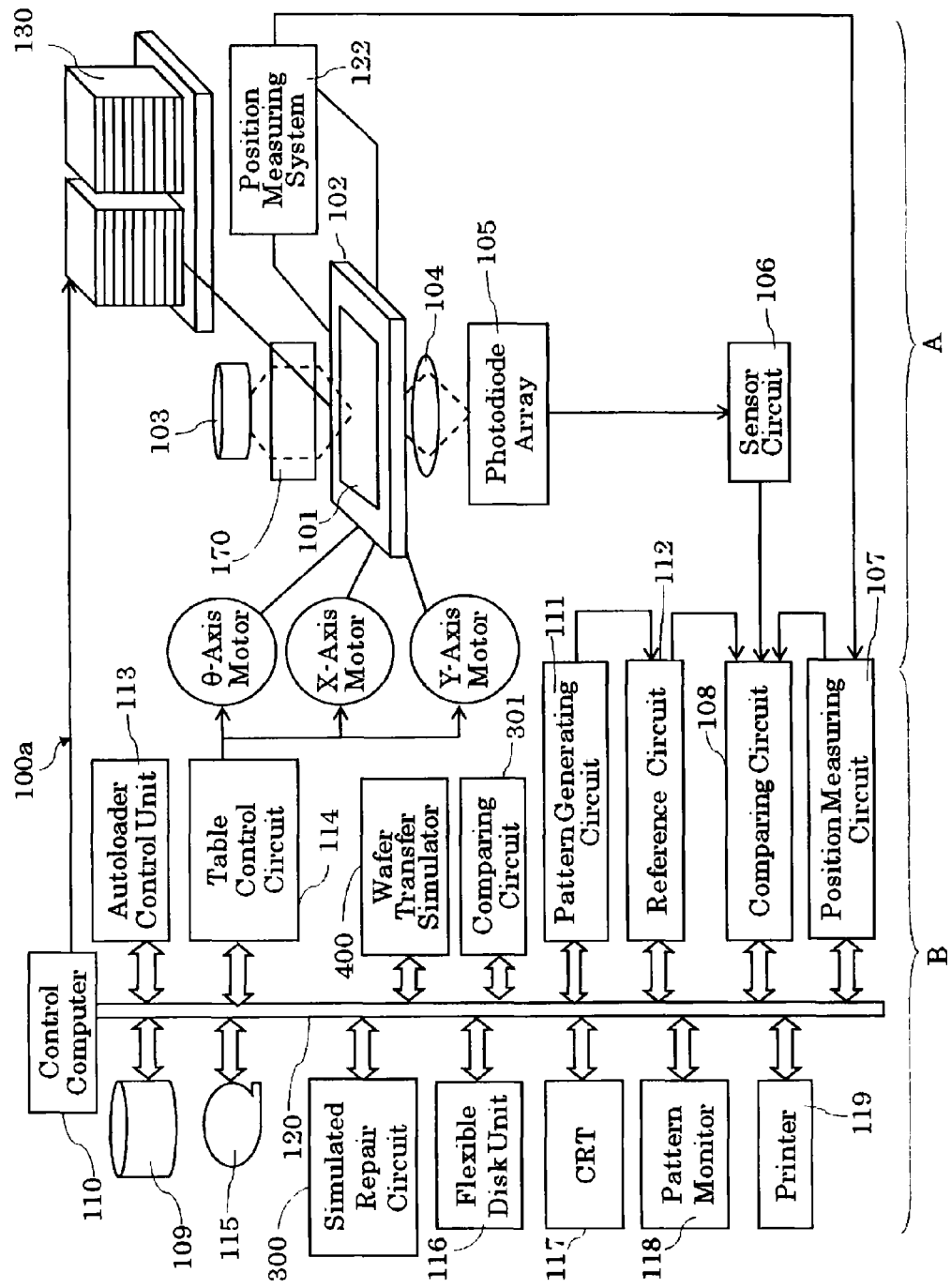
FIG. 1 is a diagram showing the configuration of an inspection system according to Embodiment 1.

FIG. 1 is a diagram showing the configuration of an inspection system according to an Embodiment of the present invention. The inspection system of the present Embodiment will be described in connection with the inspection of masks used in photolithography.

As shown in FIG. 1, the inspection system 100a includes an optical image capture unit A and a control unit B.

The optical image capture unit A includes an irradiating laser beam light source 103, an XYθ table 102 movable in the horizontal X and Y directions and rotatable in a horizontal plane (or in a θ direction), an optical illumination system 170 serving as a transmission illumination system, an enlarging optical system 104, a photodiode array 105, a sensor circuit 106, a position measuring system 122, and an autoloader 130.

In the control unit B, a control computer 110 which controls the entire inspection system 100a is connected through a bus 120 (serving as a data transmission path) to a position measuring circuit 107, a comparing circuit 108, a reference circuit 112, a pattern generating circuit 111, an autoloader control unit 113, a table control circuit 114, a storage unit 109 serving as storage units, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, for e.g., step motors.

Design pattern data which is used as reference data in database inspection is stored in the storage unit 109. This data is read out and sent to the pattern generating circuit 111 when necessary in the course of the inspection process. The pattern generating circuit 111 converts the design pattern data into image data (or bit pattern data). This image data is then sent to the reference circuit 112 for generation of reference data.

It should be noted that the inspection system of the present Embodiment may include, in addition to the components shown in FIG. 1 described above, other known components required to inspect masks. Further, although the present Embodiment is described in connection with the die-to-database inspection method, it is to be understood that the Embodiment may be applied to the die-to-die inspection method. In such a case, an optical image of one of two separate identical patterns on the mask is treated as a reference image.

Figure 2:
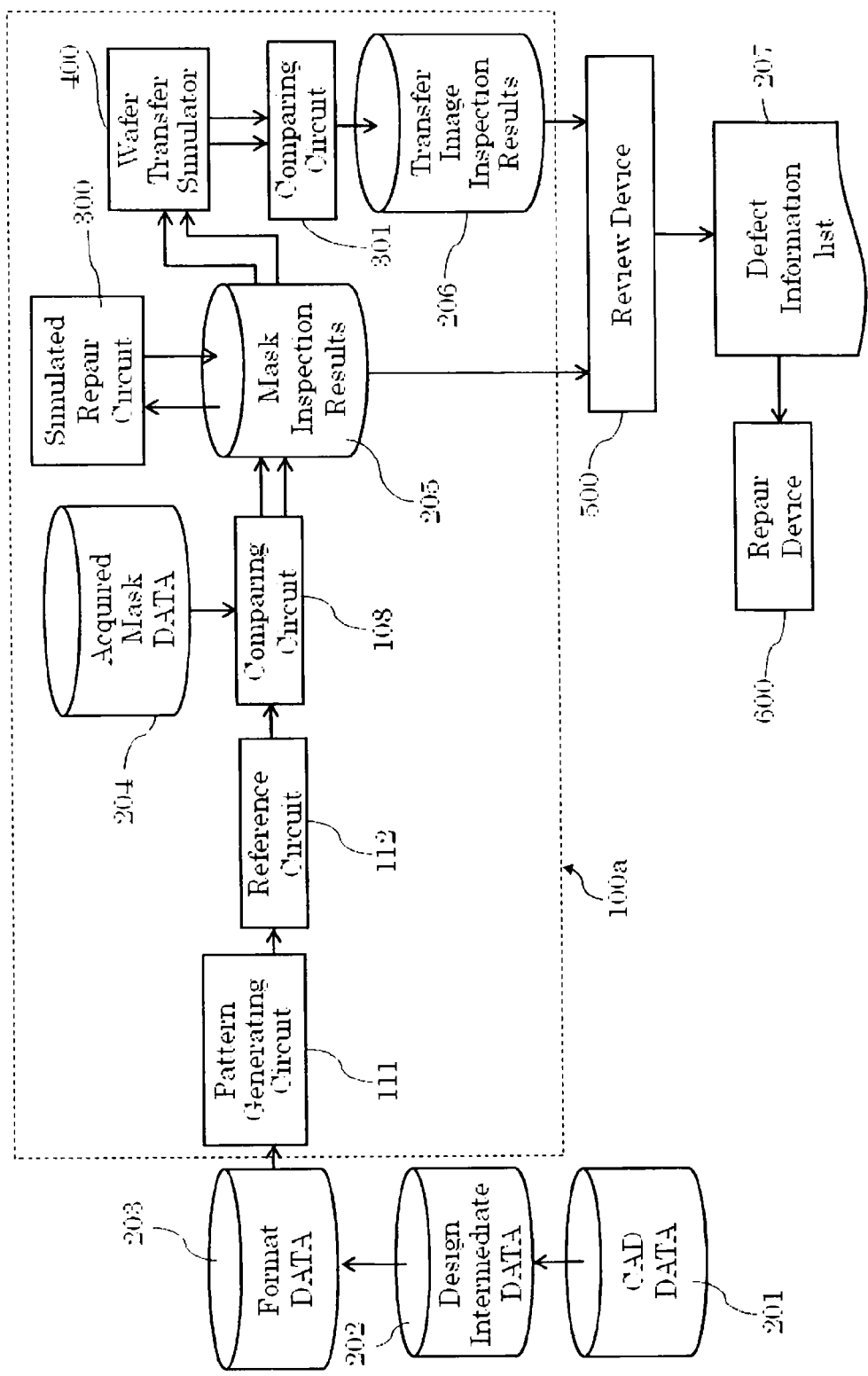
FIG. 2 is a schematic diagram showing a flow of data according to Embodiment 1.

FIG. 2 is a schematic diagram showing a flow of data according to the present Embodiment.

As shown in FIG. 2, CAD data 201 prepared by the designer (or user) is converted to design intermediate data 202 in a hierarchical format such as OASIS. The design intermediate data 202 includes data of the pattern formed on the mask created for each layer. It should be noted that, generally, writing apparatuses are not adapted to be able to directly read OASIS data. That is, each manufacturer of writing apparatus uses different format data. Therefore, OASIS data is converted, for each layer, to format data 203 in a format specific to the inspection system 100a used, and this format data 203 is input to the inspection system 100a. Although the format data 203 may be data specific to the inspection system 100a, the format data 203 may also be data compatible with a drawing device.

The format data 203 is input to the storage unit 109 of FIG. 1. The design pattern data that was used to form the pattern on the photomask 101 is stored in the storage unit 109.

The designed pattern includes pattern features each consisting of basic features such as rectangles and triangles. The storage unit 109 stores feature data indicating the shape, size, and position of each pattern feature, specifically, e.g., information such as the coordinates (x, y) of the reference position of each feature, the length of its sides, and a shape code (or identifier) identifying the type of shape such as a rectangle or triangle.

Further, a group of pattern features, defined in an area of approximately a few tens of micrometers square is referred to as a "cluster" or "cell". It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

The pattern generating circuit 111 reads design pattern data of the photomask 101 from the storage unit 109 through the control computer 110.

Specifically, upon reading the design pattern data, the pattern generating circuit 111 generates data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

The design pattern data is converted into 2-bit or other multiple-bit image data (bit pattern data). This image data is sent to the reference circuit 112. After receiving the design image data (i.e., image data of the pattern), the reference circuit 112 performs appropriate filtering on the data.

Figure 3:
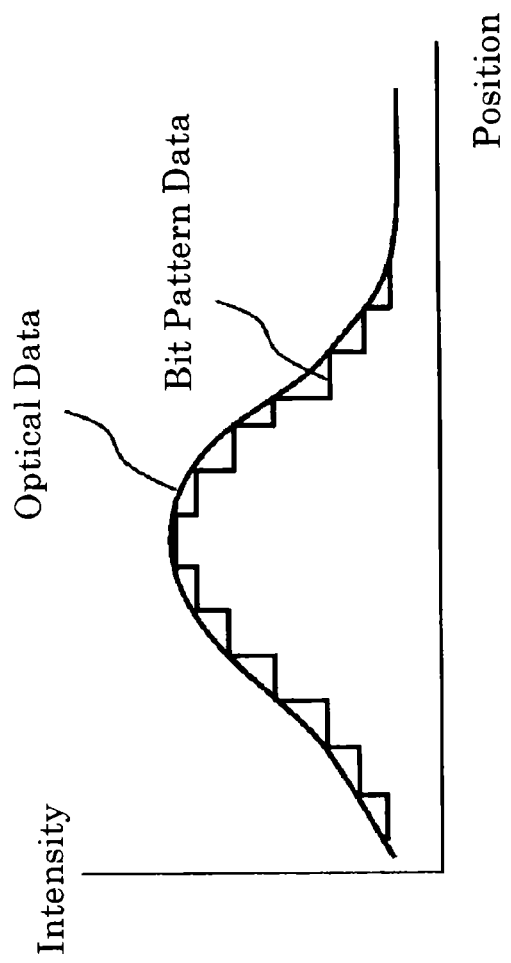
FIG. 3 is a diagram illustrating the filtering according to Embodiment 1.

FIG. 3 is a diagram illustrating the filtering.

The optical image, i.e. the acquired mask data 204, output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image to be compared with the optical image is produced.

Next, a method of obtaining the mask data 204 will be described using FIGS. 1 and 4.

The optical image capture unit A shown in FIG. 1 captures an optical image (i.e. acquired mask data 204) of a photomask 101. It will be noted that this acquired mask data 204 includes an image of a pattern on the mask, this pattern was written in accordance with the corresponding design pattern data. The detailed method of capturing this mask data 204 is as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the optical illumination system 170 and shines on the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown). Further, though not shown, the inspection system 100a may be constructed so that light is also emitted from a source below the photomask 101, and the reflected light is passed through an enlarging optical system to a second photodiode array, thus capturing the transmitted light and the reflected light simultaneously.

Figure 4:
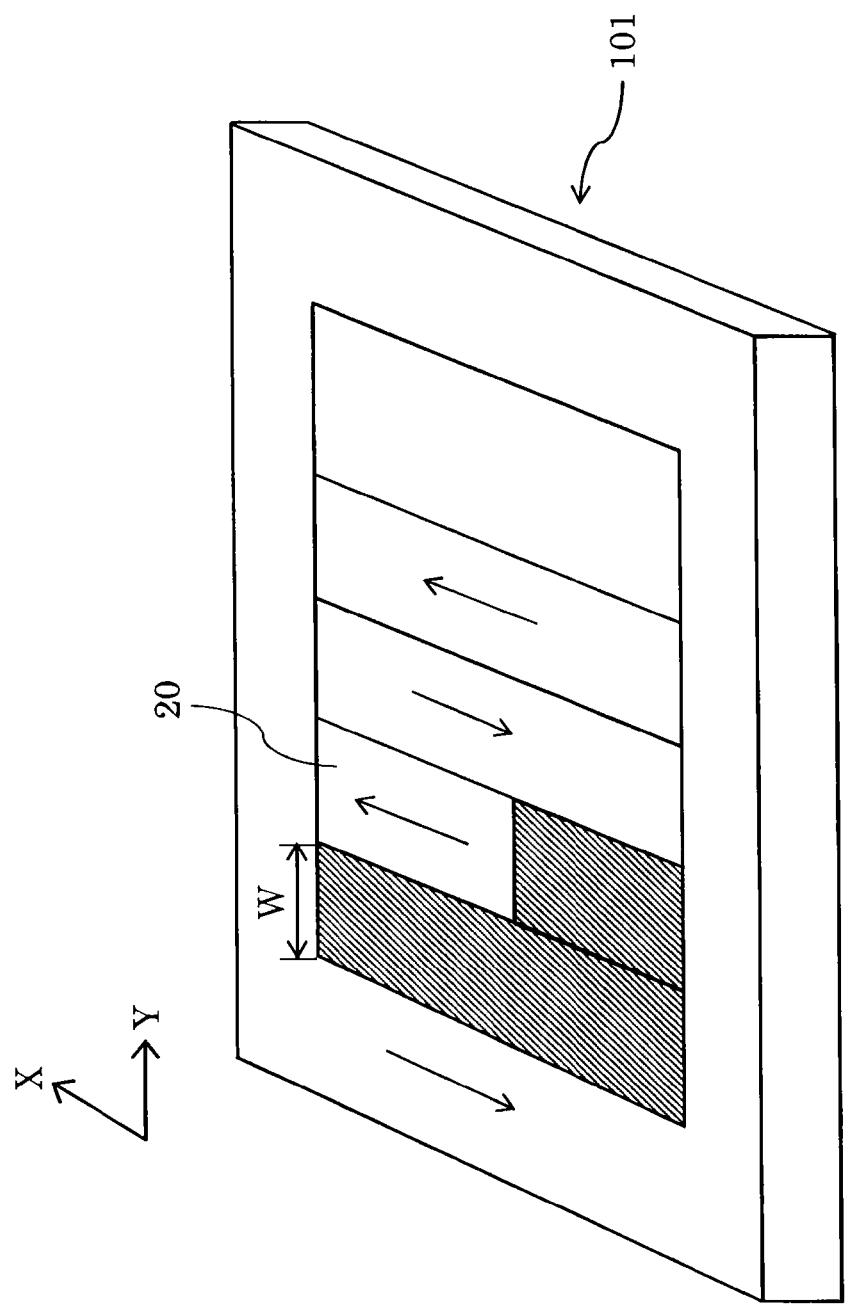
FIG. 4 is a diagram illustrating the way in which acquired mask data is captured according to Embodiment 1.

FIG. 4 is a diagram illustrating the way in which the mask data 204 is captured.

The inspection area is divided into a plurality of strip-shaped inspection stripes 20 by imaginary lines running in the X direction, where the width of each inspection stripe 20 in the Y direction is equal to the scan width W, as shown in FIG. 4. The movement of the XYθ table 102 is controlled so that each inspection stripe 20 is continuously scanned in the negative or positive X direction with the light to capture an image of the inspection stripe. At that time, the photodiode array 105 continuously generates an image (of each inspection stripe 20) having a width corresponding to the scan width W, as shown in FIG. 4. After capturing an image of the first inspection stripe 20 by scanning it, e.g., in the negative X direction, the second inspection stripe 20 is continuously scanned in the positive (i.e., opposite) X direction to capture an image of a width corresponding to the scan width W. Likewise, the third inspection stripe 20 is scanned in the negative x direction (opposite the direction in which the second inspection stripe 20 is scanned) to capture an image. This way of continuously capturing an image of one inspection stripe 20 after another reduces waste of processing time.

The pattern image formed on the photodiode array 105 as shown in FIG. 1 is photoelectrically converted by the photodiode array 105 and A/D (analog to digital) converted by the sensor circuit 106. The photodiode array 105 is made up of sensors arranged in an array. These sensors may be, e.g., TDI (Time Delay Integration) sensors. Thus, the pattern on the photomask 101 is imaged by these TDI sensors while the XYθ table 102 is continuously moved in the positive or negative X direction. It will be noted that the light source 103, the enlarging optical system 104, the photodiode array 105, and the sensor circuit 106 together form a high power optical inspection system.

The XYθ table 102 can be moved in the X and Y directions and rotated in a θ direction (or in an XY plane) by a drive system such as a 3-axis (X-Y-θ) motor driven by the table control circuit 114 under the control of the control computer 110. These X-, Y-, and θ-axis motors may be, e.g., step motors. The position of the XYθ table 102 is measured by the position measuring system 122, and the measurement data is sent to the position measuring circuit 107. Further, the photomask 101 is automatically loaded onto the XYθ table 102 from the autoloader 130 driven by the autoloader control unit 113, and, upon completion of its inspection, the photomask 101 is automatically retrieved from the XYθ table 102.

acquired mask data 204 output from the sensor circuit 106 is sent to the comparing circuit 108, i.e. first comparison unit, together with data indicative of the position of the photomask 101 on the XYθ table 102, this data is output from the position measuring circuit 107. The measurement data is, e.g., unsigned 8-bit data representing the gray scale of each pixel. The reference image is then sent to the comparing circuit 108.

The comparing circuit 108 compares each portion of the acquired mask data 204 received from the sensor circuit 106 with the corresponding portion of the reference image generated by the reference circuit 112 in accordance with a suitable comparison determination algorithm, and if the difference (e.g., in dimension) between these portions exceeds a predetermined value, the comparing circuit 108 determines that the portion of the optical image is defective. The optical image to be compared may be a transmitted image or a reflected image or a combination thereof, and the algorithm is selected to be suitable for the image to be compared. If it is determined from the comparison that a portion of the optical image is defective, then the coordinates of that portion and the acquired mask data 204 and the reference image, on which the detection of the defect is based, are stored in storage unit 109.

Incidentally, defects associated with micropatterns include not only shape defects typified by pattern edge roughness, but also pattern linewidth errors and pattern displacement errors, which are becoming more and more significant due to the miniaturization of a device pattern on a mask. Therefore, there has been a strong need to accurately control the dimensions of patterns, thus increasing the difficulty of manufacturing masks. As a result, there has been loss in the yield of masks that meet required specifications, thereby raising mask manufacturing cost. In order to address this problem, a defect evaluating method has been proposed which uses a lithography simulator. This method simulates the image which would be printed from the mask to a wafer by the photolithography apparatus and determines whether or not the pattern on the mask is defective by inspecting the simulated image. The wafer transfer simulator is a transfer image estimation part of this invention.

In the prior art inspection device, when it is determined that there is a defect, the acquired mask data used as a basis for the determination and the corresponding reference image are stored in the inspection device along with their coordinates. When the inspection of one mask is completed, an operator visually confirms a pattern at a defect portion utilizing an observation optical system in the inspection device. Then, the necessity of repair is determined. After a defect to be repaired is determined, the mask and the information required for the repair are sent to a repair device. The information required for the repair is cut-out pattern data for use in the recognition of, coordinates in the mask, discrimination between extrusion and intrusion defects, discrimination whether to remove a light-shielding film or deposit a pattern at a portion to be repaired by the repair device. The above acquired mask data can be utilized as the cut-out pattern data.

Figure 5B:
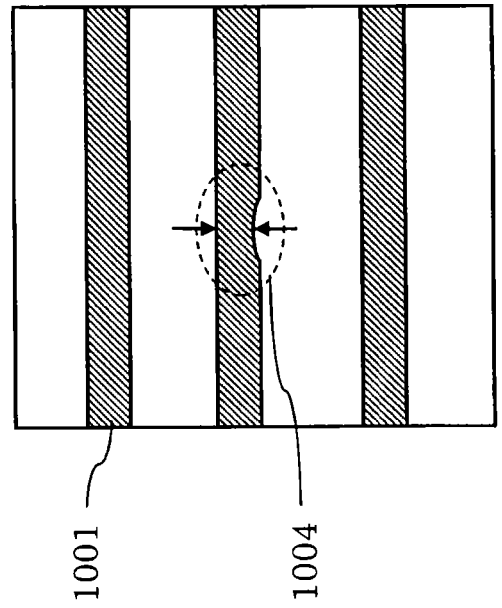
FIG. 5b is a wafer transfer image obtained by simulation of the above according to Embodiment 1.
Figure 5A:
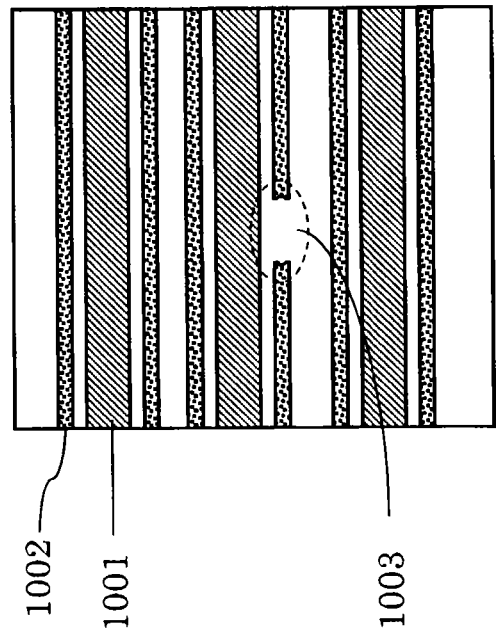
FIG. 5a is an example of the mask shape defect according to Embodiment 1.

FIG. 5*a* is an example of the mask shape defect. In this example, there is a fracture of an assist pattern 1002 in a region 1003. The assist pattern 1002 is an auxiliary pattern, which is provided in a mask for the purpose of improving the patterning characteristics of a main pattern 1001. The assist pattern 1002 itself is not transferred onto a wafer. When a wafer transfer image on the mask of FIG. 5*a* is estimated by simulation, the wafer transfer image shown in FIG. 5*b* is obtained. That is to say, in the wafer transfer image, the line width at the defect portion is smaller than the line width of a pattern at a normal portion. When the degree of reduction in the line width is more than a specified value, a region 1004 is determined as the defect portion to be repaired. The degree of reduction in the line width may be specified by a difference of an estimated line width between the normal portion and the defect portion or may be specified by the ratio of the estimated line width of the defect portion to the normal portion.

In the examples of FIGS. 5*a* and 5*b*, since the line width of the main pattern 1001 is small in a wafer transfer estimated image, it is decided to repair the line width of the main pattern 1001. However, in this case, not the main pattern 1001 but the assist pattern 1002 is repaired. That is to say, not the line width of the main pattern 1001 but the fracture of the assist pattern 1002 is repaired.

Recently, the intensity and irradiation direction of a light source used in an exposure device for forming a pattern on a mask have been optimized, and a minute pattern is formed on the mask. In this case, a very complex shaped pattern is drawn on the mask.

FIG. 6*a* is an example schematically showing a shape 1 of a surface irradiated with the exposure light source. The light intensity is uniformly distributed on the irradiated surface, and there is no directivity in the irradiation direction. The exposure light source and the mask having a pattern shape 2 shown in FIG. 6*b* are combined, and a transfer image obtained when a pattern is transferred onto a wafer is estimated. In this case, a transfer image 3 like FIG. 6*c* is obtained. In FIG. 6*c*, the line width of each pattern is uneven, and the shape will be regarded as a defect according to the decision criterion.

On the other hand, a light source having a distribution 4 in the light intensity and the directivity in the irradiation direction as shown in FIG. 7*a* and a mask having a pattern shape 5 shown in FIG. 7*b* are combined, and a pattern is transferred onto a wafer. An estimated transfer image 6 like FIG. 7*c* is obtained. The shape of the light source and the mask pattern are optimized thus, whereby a minute pattern comprising desired line width and spacing can be formed.

However, when there is a defect in the pattern of FIG. 7*b*, it is difficult to grasp a correspondence relationship between a repaired portion on a mask and an improved portion in a wafer transfer image. That is to say, an exposure image transferred from a mask to a wafer is estimated by wafer transfer simulation, and when any shape defect is detected on the exposure image, In the pattern shown in FIG. 7b, it is not easy to estimate a portion of a mask to be repaired for improving the wafer transfer image.

Figure 8A:
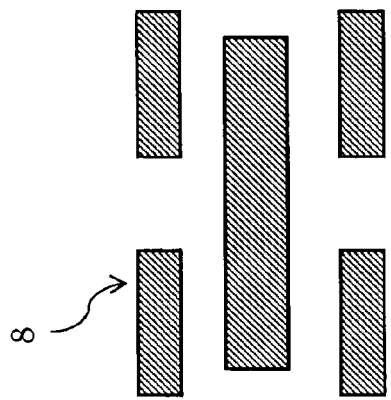
FIG. 8a is a reference image of a mask according to Embodiment 1.
Figure 8B:
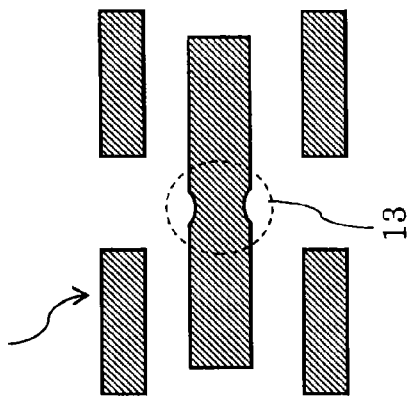
FIG. 8b is a wafer transfer image estimated from the reference image according to Embodiment 1.
Figure 9A:
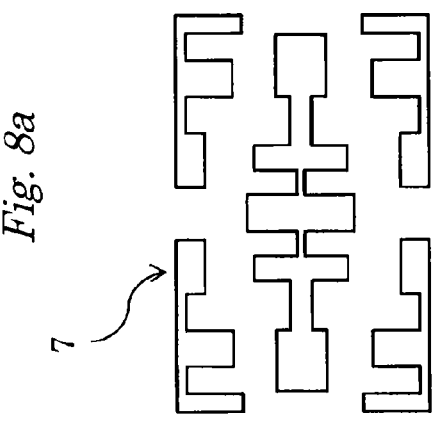
FIG. 9a is an optical image of a mask including a defect according to Embodiment 1.
Figure 9B:
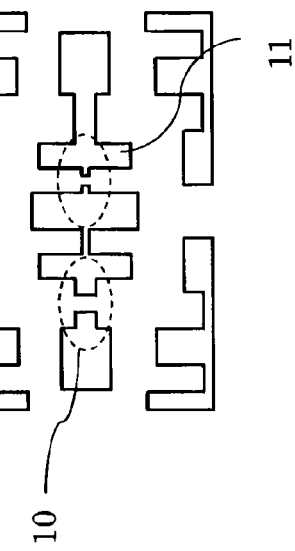
FIG. 9b is a wafer transfer image estimated from the optical image according to Embodiment 1.

FIG. 8a is a reference image of a mask. FIG. 8b is a wafer transfer image estimated from the reference image. FIG. 9a is an optical image of a mask (acquired mask data) including a defect. FIG. 9b is a wafer transfer image estimated from the optical image.

When the wafer transfer image 8 of FIG. 8b and the wafer transfer image 12 of FIG. 9b are compared, the wafer transfer image 12 has a defect portion 13 where the pattern line width is reduced. Meanwhile, when the reference image 7 of FIG. 8a and the optical image 9 of FIG. 9a are compared, the optical image 9 has two defect portions 10 and 11 where a pattern is fractured. Even if there is a plurality of defects in an optical image, in a wafer, a defect does not always occur near the coordinates corresponding to the defects. That is to say, in FIGS. 9a and 9b, although there are two defect portions in the mask, there is one defect portion in the wafer transfer image. Thus, it is difficult to estimate the correspondence relationship between the defect portions 10 and 11 and the defect portion 13. That is to say, it is difficult to estimate whether the defect portion 13 of the wafer transfer image 12 is improved by repairing any one of the defect portions 10 and 11, or whether the defect portion 13 is improved by repairing both the defect portions 10 and 11.

The larger the number of the defect portions, the more complex the correspondence relationship between the defect portion of a mask and the defect portion of a wafer transfer image. This easily occurs when the defect portions approach each other on a mask or a wafer. For example, there are three defect portions I, II and III in a mask, and there is one defect portion in a wafer transfer image. In this case, at first glance it is hard to tell which of I, II and III causes the defect in the wafer transfer image or which combination of I, II and III (such as the combination of I and II and the combination of I, II and III) causes the defect in the wafer transfer image.

When there are a plurality of defects in a mask, it is determined that repair be performed, changing the combination of the defects, a wafer transfer image is estimated from an optical image of the repaired mask, and then evaluated as to whether or not the wafer transfer image can be restored to a normal state. However, the optical image of the mask having defects has simulated repair performed in the inspection device, and if the wafer transfer image can be simulated, the repaired portion and the suitability of the level of repair can be evaluated without actual repair.

In order to simulate repair to an optical image of a mask and estimate a repaired wafer transfer image, the inspection device 100a of the present Embodiment has a simulated repair circuit 300 and a wafer transfer simulator 400. The wafer transfer simulator may be an external device of the inspection system 100a. In this case, the inspection device 100a has an interface part which can exchange data with the wafer transfer simulator, and necessary information is sent from the inspection system 100a to the wafer transfer simulator.

The flow of data in the inspection system 100a will be described using FIG. 2.

The acquired mask data of the defect portion of mask inspection results 205 is sent to the simulated repair circuit 300 to be simulated. When there are a plurality of defect portions in the acquired mask data, the repaired portion is changed, and a plurality of times of simulated repair are performed.

For example, if the repair of a defect portion can restore the wafer transfer image to a normal state, then in the repair process we should only be concerned with this specific portion. On the other hand, if an individual defect portion is repaired but the wafer optical image cannot be restored to a normal state then a combination of two portions is repaired. If any of the above combinations do not restore the wafer transfer image to a normal state then a combination of three portions are repaired. Furthermore, any combination of portions exceeding this number can be utilized in any combination to restore the wafer transfer image to its normal state. As a result we should only be concerned with the specific portions that can restore the wafer transfer image to a normal state.

When the defect coordinates on a mask approach each other, the wafer transfer image is not estimated for each defect, but the wafer transfer image is estimated for each region including the defects. That is to say, the wafer transfer image is estimated based on an optical image including all defects in a predetermined range.

For example, in the example of FIG. 9a, there are two defect portions 10 and 11. In the inspection process, these defect portions are separately detected, and the coordinates of the defect portions and the optical image are individually stored. However, the pattern of FIG. 9a is established by a combination of a plurality of patterns. These patterns influence each other to transfer one pattern onto a wafer. Thus, when the wafer transfer image is estimated, the mutual influence between a plurality of defect portions should be considered. When the wafer transfer image is estimated for each defect, a real wafer transfer image is not estimated. That is to say, it is determined that the defect portions 10 and 11 influence each other, whereby a defect of a shape that cannot be associated from the mask defect shape is transferred onto the wafer, or a pattern on the wafer not corresponding to the pattern including the defect on the mask may be affected by the defect.

The simulation of the repair to the acquired mask data is returned to the mask inspection results 205 again and thereafter sent to the wafer transfer simulator 400 along with a reference image at the corresponding portion. Instead of the reference image, an image obtained by simulating a mask production process from pattern data prior to addition of a RET pattern of mask design may be used.

In the wafer transfer simulator 400, the wafer transfer image is estimated by simulation. Specifically, the wafer transfer image is estimated from the reference image as a model, and, at the same time, the wafer transfer image is also estimated from the simulation of the acquired mask data 204. When a plurality of times of simulated repair is performed, changing the defect portion to be repaired, a plurality of the wafer transfer images are estimated from the repaired mask data 204. Thereafter, the wafer transfer images are sent from the wafer transfer simulator 400 to a comparing circuit 301 (a second comparison part).

In the comparing circuit 301, the wafer transfer image estimated from the reference image and the wafer transfer image estimated from the simulation of the acquired mask data 204 are compared with each other using an appropriate comparative determination algorithm. As the result of the comparison, when it is determined that there is a defect, the coordinate and the wafer transfer image as a basis for the defect determination are stored as transfer image inspection results 206.

In the inspection device of the present Embodiment, a wafer transfer image may be estimated by a transfer simulator without simulated repair. That is to say, as the result of the comparison in the comparing circuit 108 of FIG. 2, the coordinate at the portion determined as a defect, the optical image, and the corresponding reference image are sent to the wafer transfer simulator 400, and the wafer transfer image obtained by transferring the pattern onto a wafer is estimated. Thereafter, in the comparing circuit 301, the wafer transfer image estimated from the reference image and the wafer transfer image estimated from the optical image are compared with each other. As the result of the comparison, when it is determined that there is a defect, the coordinate and the wafer transfer image as a basis for the defect determination are stored as the transfer image inspection results 206.

In the present Embodiment, the wafer transfer image is estimated without simulated repair, and the defect on the mask and the defect on the wafer are indicated. Thereafter, the defect on the mask is simulated, and the wafer transfer image may be estimated in the simulated pattern. The wafer transfer image estimated from the reference image and the wafer transfer image estimated from the simulation of the acquired mask data 204 is compared with each other, whereby confirmation can be made as to whether or not the initially indicated defect on the wafer is eliminated.

The mask inspection results 205 and the transfer image inspection results 206 are sent to a review device 500 which is an external device of the inspection system 100a. In this review process, the operator determines whether a pattern defect found in the inspection can be tolerated. In the review device 500, an image at the defect portion of the mask is displayed while a table on which the mask is placed is moved so that the defect coordinates of defects can be observed one by one. At the same time, judgment of the defect determination, the optical image as a basis for the determination and the reference image are arranged and displayed on a screen so that the judgment, the optical image and the reference image can be confirmed. The defect on the mask and the influence on the wafer transfer image are arranged and displayed in a review process, whereby the determination whether or not the mask pattern should be repaired is facilitated. In general, projection from the mask to the wafer is performed while reduction to approximately quarter size is performed, and therefore, when images are arranged and displayed, the reduction scale has to be considered.

All defects detected by the inspection system 100a are discriminated in the review device 500. However, when the defect detected in the wafer transfer image is minor, the defect may be removed from an object to be reviewed by pre-processing.

The discriminated defect information is returned to the inspection system 100a and stored in the storage unit 109. When even one defect to be repaired is confirmed in the review device 500, the mask is sent to a repair device 600, which is an external device of the inspection system 100a, along with a defect information list 207. Since the repair method is different according to the type of the defect, that is, between the extrusion and intrusion defects, the type of the defect including determination between the extrusion and intrusion defects and the coordinate of the defect are added to the defect information list 207.

In the present Embodiment, the inspection system 100a itself may have the review function. In this case, the mask inspection results 205 and the transfer image inspection results 206 are displayed as images with incidental information of the defect determination on the screen of the control computer 110 or a screen of a separately provided calculator. The image of the mask defect portion is displayed using an observation optical system image of the inspection system 100a.

Figure 10:
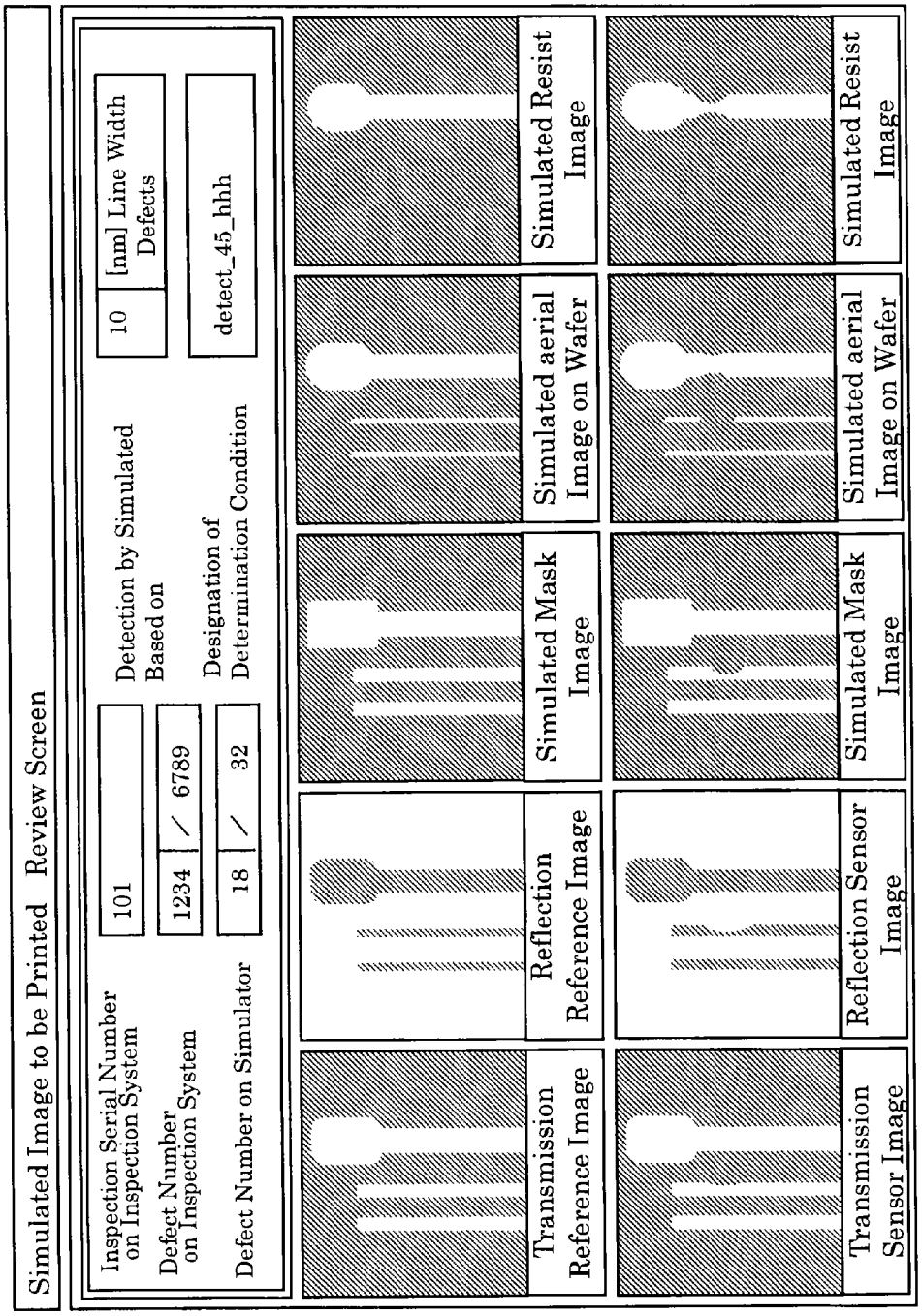
FIG. 10 is a screen through which an operator browses the results of the defect determination based on the wafer transfer image and the resist image according to Embodiment 1.

FIG. 10 is a screen through which an operator browses the results of the defect determination based on the wafer transfer image and the resist image. The upper stage, displayed on the top half of the screen, is a reference image or an optical image using a die-to-die comparison method. The lower stage, displayed on the bottom half of the screen, is an optical image including the defect. In each stage, the images are (1) an image taken by a transmission optical system of the inspection system, (2) an image taken by a reflection optical system of the inspection system, (3) a mask image estimated from these images, (4) a wafer transfer image obtained by simulating and estimating exposure conditions based on the mask image, and (5) a resist image obtained by simulating and estimating characteristics of resist in sequence from the left of FIG. 10.

According to the review screen shown in FIG. 10, since the reference image, the optical image, and the transfer image estimated from them are arranged and displayed, the operator compares these images and can locate a defect to be reviewed.

Figure 11:
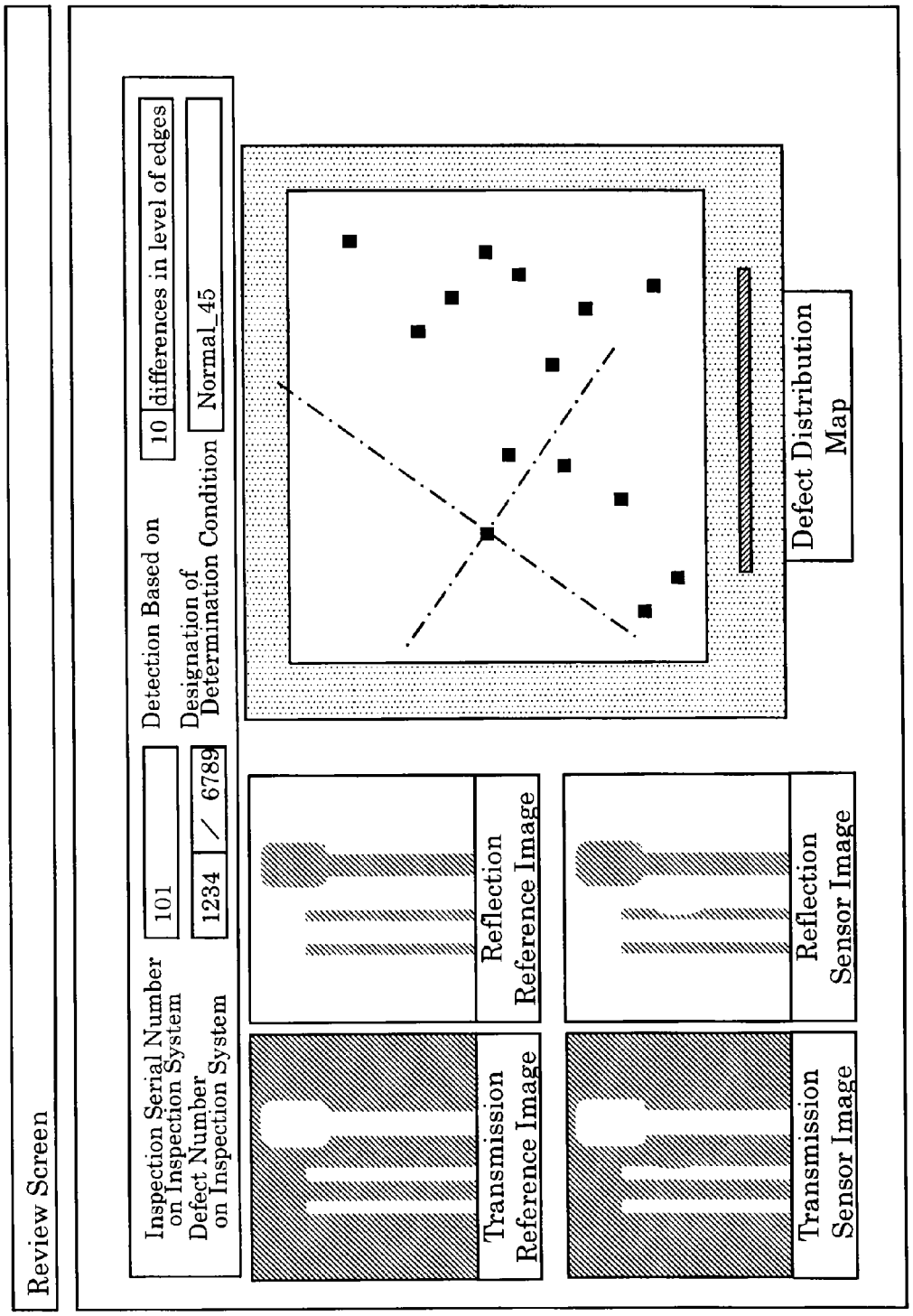
FIG. 11 shows another example of the review screen in the inspection device according to Embodiment 1.

FIG. 11 shows another example of the review screen in the inspection device. The screen consists of, a window, through which the reference image as the basis for the defect determination and the optical image including the defect are displayed so that the operator can compare the reference image and the optical image, and a window through which the defect distribution in the inspection range on the mask is displayed. There may be further provided with a profile screen window through which a difference between the optical image and the reference image is displayed, the brightness of each pixel of the optical image and the reference image are dumped and displayed with numeric values, and the sensor brightness is displayed when sectioned by the x and y axes for the purpose of analyzing the defect.

In the present Embodiment, the review screens of FIGS. 10 and 11 can be selectively displayed. The review method in this case will be described with reference to FIG. 12.

Figure 12:
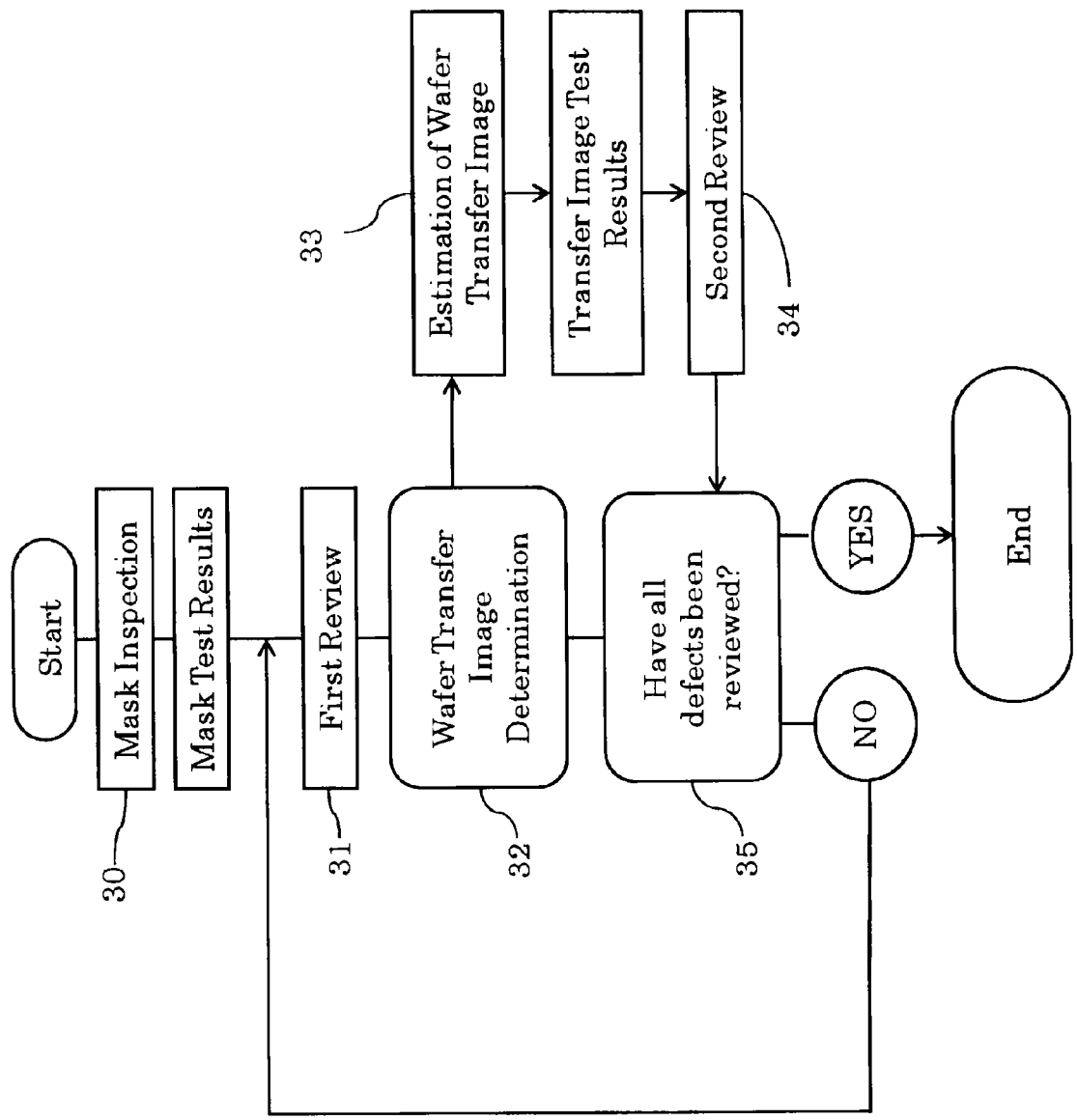
FIG. 12 is a diagram of a mask inspection review method of Embodiment 1.

Mask inspection (30) of FIG. 12 is performed by the optical image (acquired mask data) acquisition process illustrated in FIG. 2, a reference image generation process, and a comparison process. In the mask inspection (30), the acquired mask data and the reference image are compared with each other using the appropriate comparative determination algorithm. When the difference between them exceeds at least one of the threshold values, the portion is determined as the defect portion. When it is determined there is a defect, the coordinate of the defect, the acquired mask data as the basis for the defect determination, and the reference image are stored as the mask inspection results.

The mask inspection results are sent to the review device, and the necessity of repair is determined by the review of the operator (the first review (31)). In the first review (31), the review screen of FIG. 11 can be used, and the operator compares the reference image as the basis for the defect determination with the optical image including the defect and reviews. At this time, if the pattern shape formed in the mask is relatively simple, the operator does not start the wafer transfer simulator and predicts the defect portion on the wafer from the defect portion of the mask, so that the necessity of repair can be determined. Meanwhile, as illustrated in FIG. 7, when a minute pattern is formed in the mask in consideration of the combination of the pattern formed in the mask and the light source used in the exposure device, it is difficult to judge the necessity of repair without estimating the wafer transfer image.

Thus, after the first review (31), determination of the necessity of the wafer transfer image (32) is performed. When it is determined that the wafer transfer image is not required, the wafer transfer simulator is not started. Then, judgment as to whether or not all defects are reviewed (35) is performed. When all defects are not reviewed, the process returns to the first review (31). When all defects are reviewed, a series of the inspection process and the review process are terminated. Meanwhile, when it is determined that the wafer transfer image is required, the estimation of the wafer transfer image (33) is performed. As illustrated in FIG. 2, the estimation of the wafer transfer image (33) may be performed after the simulated repair of the defect portion. The transfer image inspection results are sent to the review device, and the second review (34) is performed by the operator. The review screen of FIG. 10 is used in the second review (34). That is to say, the operator compares and reviews the reference image, the optical image, and the transfer image estimated from them. Thereafter, the judgment as to whether or not all defects are reviewed (35) is performed. When all defects are not reviewed, the process returns to the first review (31). When all defects are reviewed, a series of the inspection process and the review process are terminated.

As described above, in the Embodiment 1, the wafer transfer simulator is started for each detection of the mask defect by the inspection device, and the wafer transfer image can be estimated. However, the necessity of the wafer transfer image is determined after review, and when it is judged that the wafer transfer image is required, the wafer transfer simulator may be started. The latter method is effective to examine the exposure conditions when a pattern is transferred from the mask to the wafer, for example, the degree of influence of the mask defect when the irradiance level, the light source, and so on are changed.

The features and advantages of the present invention may be summarized as follows.

According to the present Embodiment, there is provided an inspection device and an inspection method, which can facilitate the defect determination process for a mask and perform the defect determination process while estimating a defect on the mask and the resultant influence on a wafer image.

It is to be understood that the present Embodiment is not limited to the above-mentioned method and apparatus.

In this case, Unit A of the optical image data apparatus as shown in FIG. 1 can utilize an irradiating laser beam light source 103. However, optical image data can also be acquired by using an electron beam. For example, the inspection apparatus can use SEM (Scanning Electron Microscope) or MEM (Mirror Electron Microscope).

Figure 20:
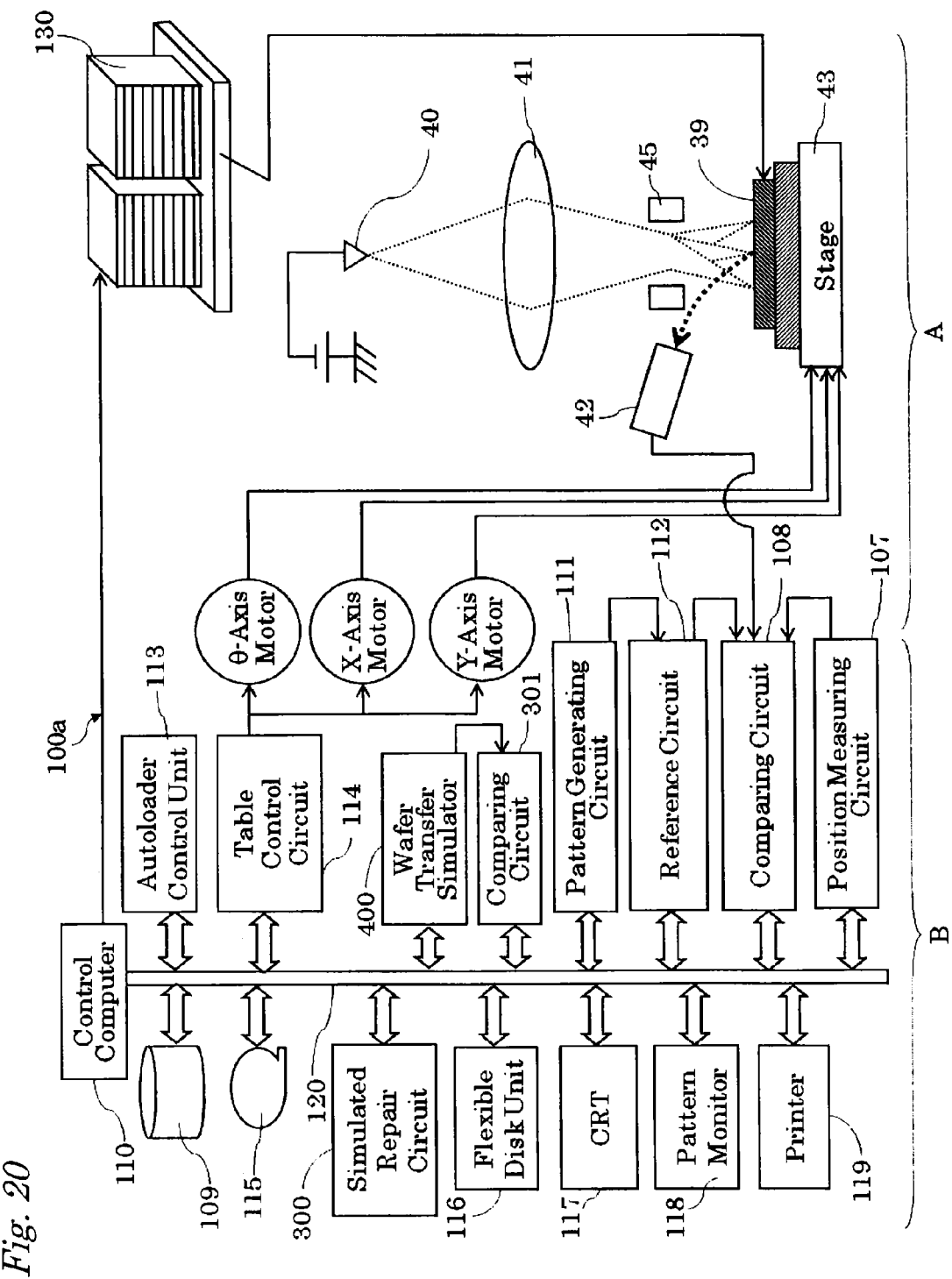
FIG. 20 is an example of optical image data acquisition using SEM (Scanning Electron Microscope) according to Embodiment 1.

FIG. 20 is an example of an inspection apparatus utilizing SEM technique. The individual components of FIG. 20 are the same as FIG. 1 and are numbered the same as in FIG. 1, with the exception of Unit A.

In the example of FIG. 20 the electron beam from the electron gun 40 is focused by the condenser lens 41 and then irradiated to the mask 39 placed on the stage 43. The movement of the scanning line and scanning speed on the mask 39 are controlled by the scanning coil 45. After the electron beam is irradiated on the mask 39, the reflected electron is guided to the detector 42. The output signal from the detector 42 is amplified by the sensor (not shown), then converted to digital data, then this signal is sent to the comparing circuit 108 (first comparison part).

Figure 21:
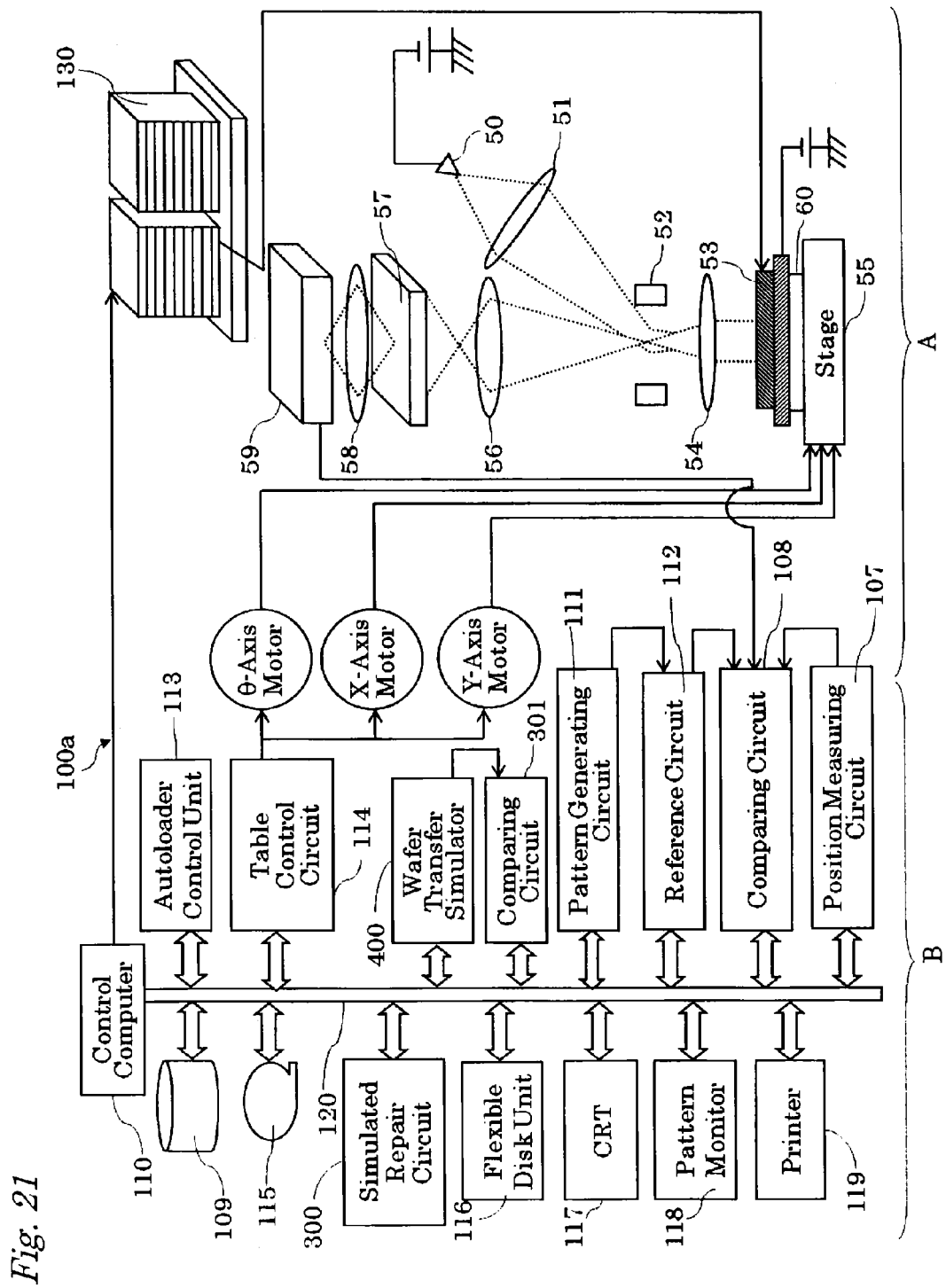
FIG. 21 is an example of optical image data acquisition using MEM (Mirror Electron Microscope) according to Embodiment 1.

FIG. 21 is another example using MEM to acquire optical image data as in Unit A of FIG. 1. The individual components of FIG. 21 are the same as FIG. 1 and are numbered the same as in FIG. 1, with the exception of Unit A.

As shown in FIG. 21. The mask 53 is placed on an insulated material 60 on the stage 55. The electron beam from the electron beam gun 50 is focused by the condenser lens 51, then deflected by the ExB deflector 52, after, the electron beam passes through the objective lens 54 forming an expanded beam which reaches the mask 53 vertically. After the electron beam is irradiated on the mask 53, the reflected beam is transmitted through the objective lens 54 to the focus lens 56 and then is projected on to the fluorescent screen 57. The optical image on the fluorescent screen 57 is focused on to the light receiving surface of CCD 59 by an optical lens 58. Then, the image of pattern focused on the CCD 59 is transformed into the digital data, then sent to the comparing circuit 108 (first comparing unit).

The above description of the present Embodiment has not specified apparatus constructions, control methods, etc. which are not essential to the description of the invention, since any suitable apparatus constructions, control methods, etc. can be employed to implement the invention. Further, the scope of this invention encompasses all pattern inspection systems and pattern inspection methods employing the elements of the invention and variations thereof which can be designed by those skilled in the art.

Embodiment 2

FIG. 5a is an example of the mask shape defect. In this example, there is a fracture of an assist pattern 1002 in a region 1003. The assist pattern 1002 is a pattern, which is auxiliary provided in a mask for the purpose of improving the patterning characteristics of a main pattern 1001. The assist pattern 1002 itself is not transferred onto a wafer. When a wafer transfer image on the mask of FIG. 5a is estimated by simulation, the wafer transfer image shown in FIG. 5b is obtained. That is to say, in the wafer transfer image, the line width at the defect portion is smaller than the line width of a pattern at a normal portion. When the degree of reduction in the line width is more than a specified value, a region 1004 is determined as the defect portion to be repaired. The degree of reduction in the line width may be specified by a difference of an estimated line width between the normal portion and the defect portion or may be specified by the ratio of the estimated line width of the defect portion to the normal portion.

In the examples of FIGS. 5a and 5b, since the line width of the main pattern 1001 is small in a wafer transfer estimated image, it is determined to repair the line width of the main pattern 1001. However, in this case, not the main pattern 1001 but the assist pattern 1002 is repaired. That is to say, not the line width of the main pattern 1001 but the fracture of the assist pattern 1002 is repaired.

Recently, the intensity and the irradiation direction of a light source used in an exposure device for forming a pattern on a mask have been optimized, and a minute pattern can be formed in the mask. In this case, a very complex shaped pattern can be drawn on the mask.

FIG. 6a is an example schematically showing a shape of a surface irradiated with the exposure light source. The light intensity is uniformly distributed in the irradiated surface, and there is no directivity in the irradiation direction. The exposure light source and the mask having a pattern shape shown in FIG. 6b are combined, and a transfer image obtained when a pattern is transferred onto a wafer is estimated. In this case, a transfer image like FIG. 6c is obtained. In FIG. 6c, the line width of each pattern is uneven, and the shape will be regarded as a defect according to the decision criterion.

On the other hand, a light source having a distribution in the light intensity and the directivity in the irradiation direction as shown in FIG. 7a and a mask having a pattern shape shown in FIG. 7b are combined, and a pattern is transferred onto a wafer. An estimated transfer image like FIG. 7c is obtained. The shape of the light source and the mask pattern are optimized thus, whereby a minute pattern comprising desired line width and spacing can be formed.

However, when there is a defect in the pattern of FIG. 7b, it is difficult to grasp a correspondence relationship between a repaired portion on a mask and an improved portion in a wafer transfer image. That is to say, an exposure image transferred from a mask to a wafer is estimated by wafer transfer simulation, and when any shape defect is detected on the exposure image, In the pattern shown in FIG. 7b, it is not easy to estimate a portion of a mask to be repaired for improving the wafer transfer image.

FIG. 8a is a reference image of a mask. FIG. 8b is a wafer transfer image estimated from the reference image. FIG. 9a is an optical image of a mask (acquired mask data) including a defect. FIG. 9b is a wafer transfer image estimated from the optical image.

When the wafer transfer image 8 of FIG. 8b and the wafer transfer image 12 of FIG. 9b are compared, the wafer transfer image 12 has a defect portion 13 where the pattern line width is reduced. Meanwhile, when the reference image 7 of FIG. 8a and the optical image 9 of FIG. 9a are compared, the optical image 9 has two defect portions 10 and 11 where a pattern is fractured. Even if there is a plurality of defects in an optical image, in a wafer, a defect does not always occur near the coordinates corresponding to the defects. Namely, in FIGS. 9a and 9b, although there are two defect portions in the mask, there is one defect portion in the wafer transfer image. Thus, it is difficult to estimate the correspondence relationship between the defect portions 10 and 11 and the defect portion 13. That is to say, it is difficult to estimate whether the defect portion 13 of the wafer transfer image 12 is improved by repairing any one of the defect portions 10 and 11, or whether the defect portion 13 is improved by repairing both the defect portions 10 and 11.

The larger the number of the defect portions, the more complex the correspondence relationship between the defect portion of a mask and the defect portion of a wafer transfer image. This easily occurs when the defect portions approach each other on a mask or a wafer. For example, there are three defect portions I, II and III in a mask, and there is one defect portion in a wafer transfer image. In this case, at first glance it is hard to tell which of I, II and III causes the defect in the wafer transfer image or which combination of I, II and III (such as the combination of I and II and the combination of I, II and III) causes the defect in the wafer transfer image.

When there are a plurality of defects in a mask, it is determined that repair is to be performed, changing the combination of the defects, a wafer transfer image is estimated from an optical image of the repaired mask, and whether or not the wafer transfer image is restored to a normal state is confirmed. However, the optical image of the mask having defects is simulated in the inspection device, and if the wafer transfer image can be simulated, the repaired portion and the suitability of the level of repair can be evaluated without actual repair. If this function is provided to an inspection device, the inspection device is capable of indicating the level of influence which the mask defect exerts on a wafer, or which pattern on the mask should be repaired to eliminate the detected defect.

Hereinafter, each aspect of the present Embodiment will be described with reference to the drawings.

(1) Defect Estimation Device and Defect Estimation Method

Figure 13:
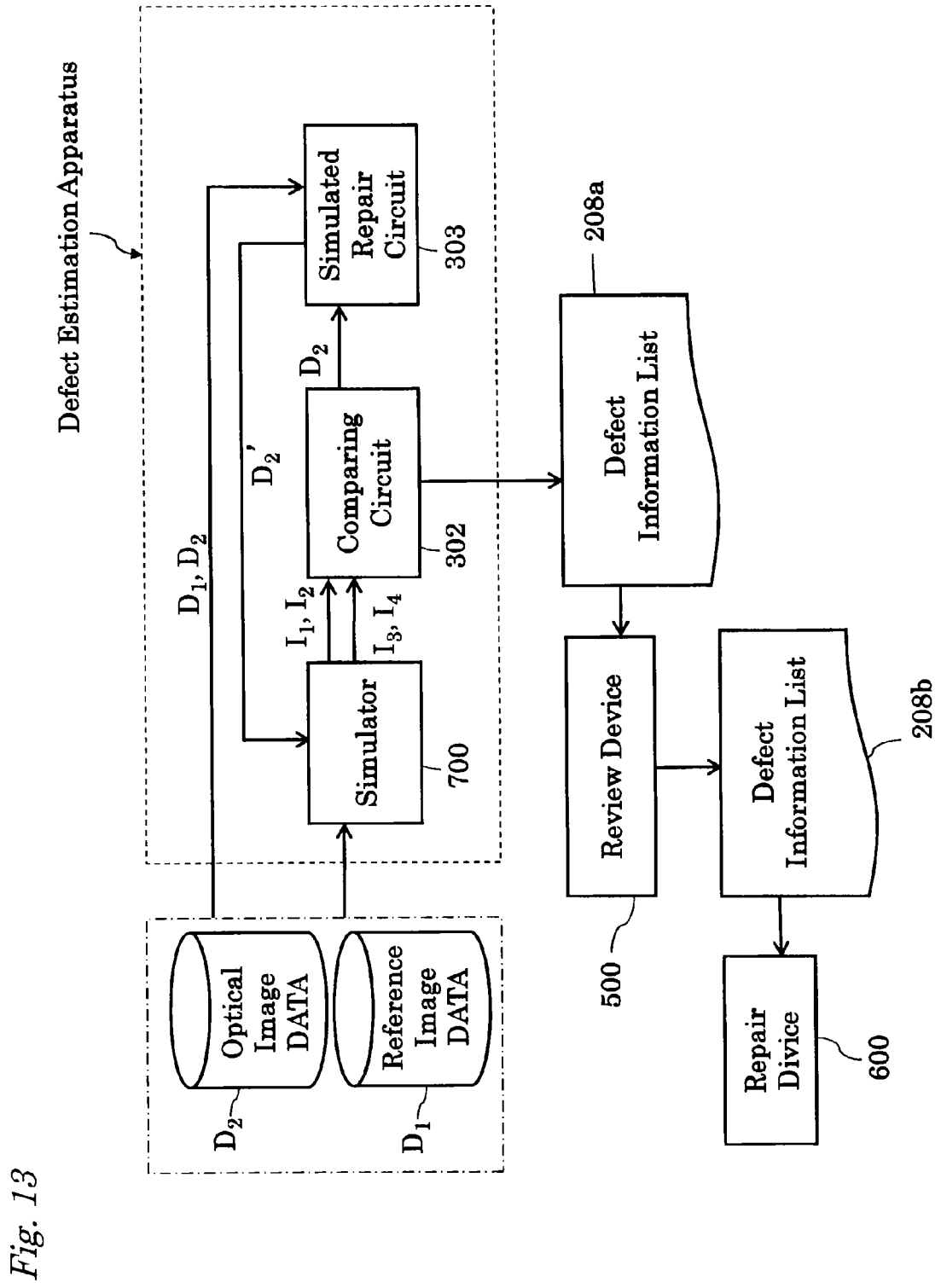
FIG. 13 shows a defect estimation device and a defect estimation method according to Embodiment 2.

A defect estimation device and a defect estimation method according to a first aspect of the Embodiment 2 will be described with reference to FIG. 13. A portion surrounded by a dot line in FIG. 13 is a main portion constituting the defect estimation device.

The defect estimation device has a simulator (also referred to as an estimation part, and the same in the present application) 700, a comparing circuit 302, and a simulated repair circuit 303. Reference image data $D_1$ and optical image data $D_2$ are input to the simulator 700. This data can be generated in the inspection device as described in the Embodiment 2.

The simulator 700 estimates a pattern image to be transferred from the mask to the wafer, using the reference image data $D_1$ and the optical image data $D_2$. The pattern image may be a resist pattern image at any stage in a series of a lithography process such as development and etching or may be a circuit pattern image finally formed in the wafer. The wafer is an example of a substrate in this invention.

For example, a photo mask formed with a predetermined circuit pattern is a test object. The photo mask is used for transferring the circuit pattern onto a wafer. The transfer is performed by the following process, for example. First, a resist film is provided on the wafer. Next, the wafer is exposed by an exposure device through the photo mask to transfer an exposure image of the circuit pattern to the resist film. Then, the resist film is developed to form a resist pattern. Thereafter, a lower film is etched using the resist pattern as a mask, and after that, the resist film is peeled. By doing this, the lower film can be processed to a pattern having a desired shape. Next, copper (Cu) or the like is filled in a recess of the lower film, and thereafter, an unnecessary portion is removed by a CMP (Chemical Mechanical Planarization) method, whereby a wiring pattern is formed.

In the above example, the simulator 700 can estimate the exposure image to be transferred from the mask to the wafer by the exposure device and can also estimate a resist pattern image to be formed on the wafer. Alternatively, the simulator 700 can estimate a pattern image of the recess to be formed in the lower film and a wiring pattern image after being filled with copper and the like. These pattern images include a pattern image $I_1$ estimated from the reference image data $D_1$ and a pattern image $I_2$ estimated from the optical image data $D_2$. In the present Embodiment, images estimated by the simulator 700, that is, the exposure image transferred from the mask to the wafer by the exposure image, the resist pattern image formed on the wafer, the wiring pattern image, and so on are collectively referred to as pattern images and are discriminated from the reference image data $D_1$ and the optical image data $D_2$.

The simulation can be performed, for instance, as stated below.

<Simulation of Exposure Image>

As the simulation of the exposure image such as the circuit pattern transferred onto the wafer by the exposure device, Non-Patent Document 3 (H. H. Hopkins, On the di_reaction theory of optical images, In Proc. Royal Soc. Series A., volume 217 No. 1131, pages 408-432, 1953) and N. B Cobb, (Fast Optical and Process Proximity Correction Algorithms for Integrated Circuit Manufacturing) A dissertation submitted in partial satisfaction of the requirements for the degree of Doctor Of Philosophy in Engineering: Electrical Engineering and Computer Science in the Graduate Division of the University of California in Berkeley, Spring 1988 can be referred to.

An optical system of the exposure device is a partially coherent optical system. When a pattern drawn on a mask by the exposure device is transferred onto a wafer, light intensity I(x, y) at a point (x, y) on the wafer can be calculated using the following formula by obtaining the Fourier transformed quantity $I^*(f_x, f_y)$. i is a pure imaginary number, and $i=(-1)^{1/2}$.

$$I(x, y) = \iint I^*(f_x, f_y) \exp\{-2\pi i (f_x x + f_y y)\} df_x df_y$$

$I^*(f_x, f_y)$ can be obtained using the following Hopkings formula:

$$I^*(f_x, f_y) = \iint T(f_x + f_x', f_y + f_y'; f_x', f_y') \times G(f_x + f_x', f_y + f_y') \times G^*(f_x', f_y') df_x' df_y'$$

In the Hopkins formula, $G(f_x, f_y)$ represents the Fourier transformed quantity of the mask. $T(f_x', f_y'; f_x, f_y)$ represents transmission cross coefficients and is calculated as follows:

$$T(f_x',f_y';f_x'',f_y'') = \iint J_0^-(f_x,f_y) \times K(f_x+f_x',f_y+f_y'') \times K^*(f_x+f_x'', f_y+f_y'') df_x df_y$$

In the above formula, $J_0^-(f_x, f_y)$ represents light source intensity distribution in an effective source. $K(f_x, f_y)$ represents a pupil function (coherent transmission function). In a mask optimized by changing the shape of the light source by SMO (source mask optimization), the change of the shape of the light source is reflected in the light source intensity distribution $J_0^-(f_x, f_y)$.

<Simulation of Resist Pattern from Exposure Image>

As the simulation of the resist pattern from the exposure image, Non-Patent Document 4 (N. B. Cobb, A. Zakhor, M. Reihani, F. Jahansooz, and V. N. Raghavan: Proc. SPIE 3051 (1997) 458) and N. B Cobb, (Fast Optical and Process Proximity Correction Algorithms for Integrated Circuit Manufacturing) A dissertation submitted in partial satisfaction of the requirements for the degree of Doctor Of Philosophy in Engineering: Electrical Engineering and Computer Science in the Graduate Division of the University of California in Berkeley, Spring 1988 can be referred to.

Figure 14:
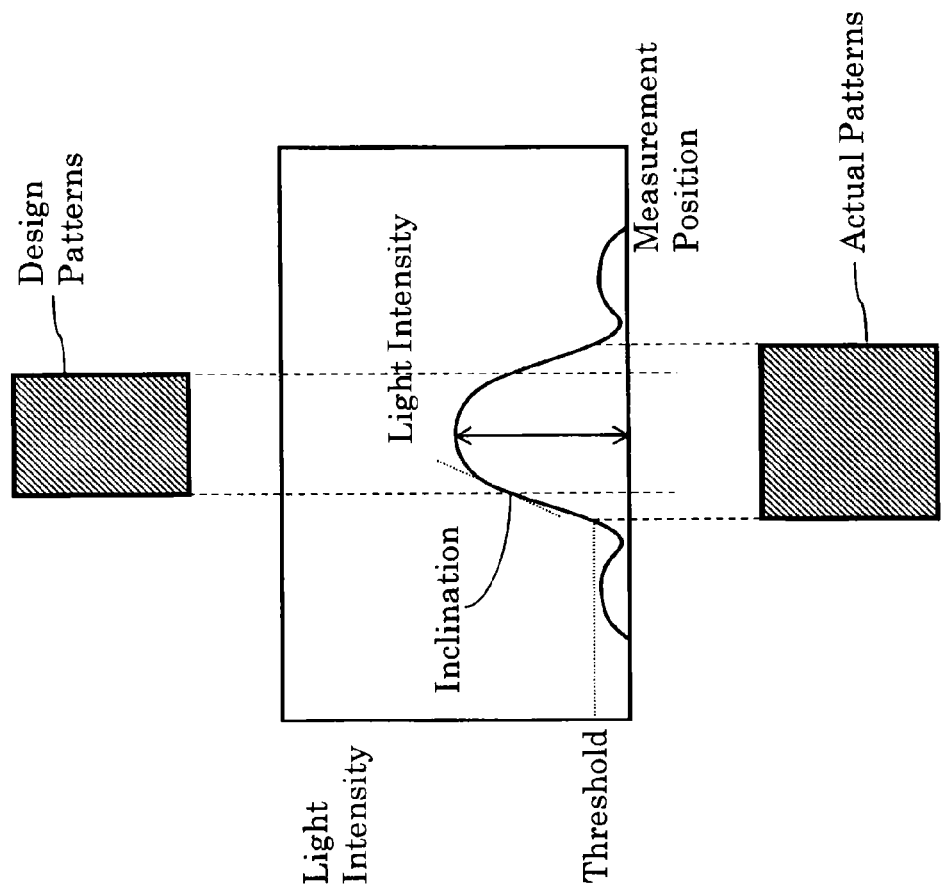
FIG. 14 is a diagram showing the method of simulating the resist pattern of Embodiment 2.

The method described in the Non-Patent Document 4 is as follows. First, a plurality of design patterns are previously provided to be transferred and developed, the finished resist pattern is measured, a light intensity distribution when each pattern is transferred by the exposure device is obtained by the simulation of the exposure image. FIG. 14 shows one such example.

As shown in FIG. 14, with regard to each pattern, (1) light intensity and (2) inclination of the light intensity at the edge of the design pattern are obtained from exposure amount distribution. Since the measurement result of the corresponding finished pattern shows the position of the side of a figure, the light intensity corresponding to the position is obtained. The light intensity is a threshold value determining the position of the side of a pattern and is function of (1) the light intensity and (2) the inclination of the light intensity at the edge of the design pattern.

Table 1 is one such example.

TABLE 1

|  | Light Intensity | | |
| --- | --- | --- | --- |
|  | 1.00 | 0.95 | 0.90 |
| Inclination 1.00 | 1.00 | 0.99 | 0.98 |
| 0.95 | 0.99 | 0.98 | 0.97 |
| 0.90 | 0.99 | 0.98 | 0.97 |

The actual simulation is performed as follows. The optical distribution for the pattern to be simulated in a resist shape is obtained by the exposure image simulation, and the light intensity and the inclination at the position of the side are obtained. The threshold value of the light intensity is obtained from the light intensity distribution and the inclination, using the relationship shown in the table 1. Then, the position of the side is calculated from the optical distribution, obtained by the exposure image simulation, and the threshold value. Accordingly, since the movement of the position of the side is shown, the finished pattern can be simulated.

<Simulation of Pattern Shape after Wafer Process Processing Such as Etching>

In a manufacturing process of LSI, a resist pattern is formed on a wafer. Thereafter, a lower film is etched using the resist pattern as a mask to form a pattern having a desired shape in the lower layer. When a multilayer wiring structure is formed by a damascene method, the lower film is used as an insulating film, and a conductive barrier film and a copper main conductive film are filled in a recess of the insulating film after etching to form a copper wiring pattern.

As described above, in a series of the LSI manufacturing process, various patterns other than the resist pattern are formed. As for the simulation of the patterns, Non-Patent Document 5 (M. Osawa, T. Yao, H. Aoyama, K. Ogino, H. Hoshino, Y. Machida, S. Asai, and H. Arimoto, J. Vac. Sci. Technol. B21 (2003) 2806) and N. B Cobb, (Fast Optical and Process Proximity Correction Algorithms for Integrated Circuit Manufacturing) A dissertation submitted in partial satisfaction of the requirements for the degree of Doctor Of Philosophy in Engineering: Electrical Engineering and Computer Science in the Graduate Division of the University of California in Berkeley, Spring 1988 can be referred to.

According to the Non-Patent Document 5, a point (x, y) on a side is moved by $\delta(x, y)$ outward and perpendicularly to the side, the movement amount is represented by the following formula:

$$\delta l(x, y) = \gamma \int_{Pattern} g(x - x', y - y') dx' dy' + f(L)$$

In the above formula, L is a size of a figure to which a noticing point on a side belongs. f(L) in the second term is the movement amount of the point (x, y) determined by the size of the figure. The first term is the movement amount at the point (x, y) generated by the influence of the figure to which the noticing point belongs and the surrounding figure. The first term contributes to the description in the Non-Patent Document 5. $\gamma$ is an indication of the ratio of the movement amount changing depending on a pattern. g(x, y) is specified as follows:

$$\int_A g(x) dx = \int_{-\infty}^{\infty} \int_{-\infty}^{\infty} g(x, y) dx dy = 1$$

Since the above functions and the parameter $\gamma$ are different according to a material, processing method, and processing time of a film which is an object subjected to, for example, etching, they are previously determined by experiment. Accordingly, since the movement of the position of the side is shown, the finished pattern can be simulated.

By virtue of the above simulation method, the pattern images $I_1$ and $I_2$ estimated by the simulator 700 are sent to the comparing circuit 302. In the comparing circuit 302, the pattern image $I_1$ estimated from the reference image data $D_1$ and a pattern image $I_2$ estimated from the optical image data $D_2$ are compared with each other using the appropriate comparative determination algorithm. For example, in the resist pattern, the information of patterns to be described respectively in the pattern images $I_1$ and $I_2$ are compared, and when the difference between the positions of the corresponding sides is more than a predetermined level, for example, 4 nm, it is regarded that there is a defect. As the result of the comparison, when it is determined that there is a defect, the coordinate and the pattern images $I_1$ and $I_2$ as the basis for the defect determination are stored in the comparing circuit 302. For example, in FIG. 9b, the defect portion of the pattern image $I_2$ is indicated by reference numeral 13.

With regard to the portion determined as a defect based on the pattern images $I_1$ and $I_2$, the reference image data $D_1$ at the corresponding position of the mask and the optical image data $D_2$ are sent to the simulated repair circuit 303. In the simulated repair circuit 303, simulated repair is applied to the defect portion sent to the simulated repair circuit 303. simulated repair is performed as follows. The reference image data $D_1$ of the mask and the optical image data $D_2$ are compared with each other, and different positions are found around the position estimated as a defect. The optical information at the different position is replaced with the corresponding optical information of the reference image. For example, the information of the defect portion indicated by reference numeral 10 in FIG. 9a is replaced with the information of the defect portion denoted by reference numerals 701 and 702 in FIG. 7b. When there are a plurality of defect portions in the pattern image $I_2$, the repaired portion is changed, and a plurality of times of simulated repair are performed, whereby a defect that will cause a pattern error can be specified.

For example, if the repair of a defect portion can restore the wafer transfer image to a normal state, then in the repair process we should only be concerned with this specific portion. On the other hand, if an individual defect portion is repaired but the wafer optical image cannot be restored to a normal state, then a combination of two portions is repaired. If any of the above combinations do not restore the wafer transfer image to a normal state then a combination of three portions are repaired. Furthermore, any combination of portions exceeding this number can be utilized in any combination to restore the wafer transfer image to its normal state.

When contiguous defect coordinates are stored as optical image data $D_2$ in the comparing circuit 302, in the simulated repair circuit 303, simulated repair is performed for each region including the defects. That is, the optical image data $D_2$ including all defects in a predetermined range is simulated.

For example, in the example of FIG. 9a, there are the two defect portions 10 and 11. The defect portions are separately detected in the comparing circuit 302, and the coordinates of the defect portions and the pattern image $I_2$ are individually stored. However, the pattern of FIG. 9a is established by a combination of a plurality of patterns. These patterns influence each other to transfer on pattern onto a wafer. Thus, when the pattern image $I_2$ is estimated, the mutual influence between a plurality of defect portions should be considered. When the pattern image $I_2$ is estimated for each defect, a real pattern image $I_2$ is not estimated. That is to say, it is determined that the defect portions 10 and 11 influence each other, whereby a defect of a shape that cannot be associated from the mask defect shape is transferred onto the wafer, or a pattern on the wafer not corresponding to the pattern including the defect on the mask is affected by the defect.

The simulated optical image data $D_2$ as new optical image data $D_2'$ is returned to the simulator 700 again. In the simulator 700, a new pattern image $I_3$ is estimated from the reference image data $D_1$ as a model, and a new pattern image $I_4$ is also estimated from the simulated optical image data $D_2'$. When a plurality of times of simulated repair are performed changing the defect portion to be repaired, a plurality of the new pattern images $I_4$ estimated from the repaired optical image data $D_2'$ are obtained.

The pattern images $I_3$ and $I_4$ may be at the same stage of the lithography process as the pattern image $I_1$ and $I_2$ or may be in the more advanced state than the pattern image $I_1$ and $I_2$. For example, all the pattern images $I_1$, $I_2$, $I_3$ and $I_4$ may be exposure images transferred from the mask to the wafer by the exposure device. When the pattern images $I_1$ and $I_2$ are resist pattern images formed on the wafer, the pattern images $I_3$ and $I_4$ may be wiring pattern images formed on the wafer.

The pattern images $I_3$ and $I_4$ newly estimated by the simulator 700 are sent from the simulator 700 to the comparing circuit 302 again. The pattern image $I_3$ as a model and the pattern image $I_4$ after repair are compared with each other, whereby confirmation can be made as to whether or not the initially indicated defect on the wafer is eliminated. As the result of the comparison, the coordinate determined as a defect and the pattern images $I_3$ and $I_4$ as the basis for the defect determination are output as a defect information list 208a to an external device along with the reference image data $D_1$ and the optical image data $D_2$.

In the present Embodiment, the defect information list 208a is sent to the review device 500. In this review process, the operator determines whether a pattern defect found in the inspection can be tolerated. In the review device 500, an image at the defect portion of the mask is displayed while a table on which the mask is placed is moved so that the defect coordinates of defects can be observed one by one. At the same time, judgment of the defect determination, pattern image $I_3$ and $I_4$, reference image data $D_1$ and optical image data $D_2$ used as a basis for the determination and the reference image are arranged and displayed on a screen so that judgment, the optical image and the reference image can be confirmed. The defect on the mask and the influence on the wafer transfer image are arranged and displayed in a review process, whereby the determination whether or not the mask pattern should be repaired is facilitated. In general, projection from the mask to the wafer is performed while reduction to approximately quarter size is performed, and therefore, when images are arranged and displayed, the reduction scale is considered.

When even one defect to be repaired is confirmed in the review device 500, the mask is sent to a repair device 600, which is an external device of the inspection system 100a, along with a defect information list 208b. Since the repair method is different according to the type of the defect, for example, between the extrusion and intrusion defects, the type of the defect including discrimination between the extrusion and intrusion defects and the coordinate of the defect are added to the defect information list 208b.

As described above, in the defect estimation device and the defect estimation method in the first aspect of Embodiment 2, the pattern image after being transferred from the optical image to the wafer is estimated to be compared with the pattern image estimated from the reference image in a similar manner, whereby the presence of defect is determined. After the simulated repair of the pattern image at the portion determined as a defect, the pattern image is compared with the image as a model again, and the presence of defect is determined. Accordingly, the defect on the mask, the influence of the defect on the wafer, and the degree of the improvement by the repair can be estimated.

In the defect estimation device and the defect estimation method in the first aspect of Embodiment 2, although the reference image is a standard image, it is not limited thereto. The standard image may be a reference image created from design data of a pattern or an optical image having the same pattern in a region different from the optical image which is an object on a mask.

(2) Inspection Device

An inspection device according to a second aspect of Embodiment 2 is characterized by including the function of the defect estimation device according to the first aspect.

Figure 15:
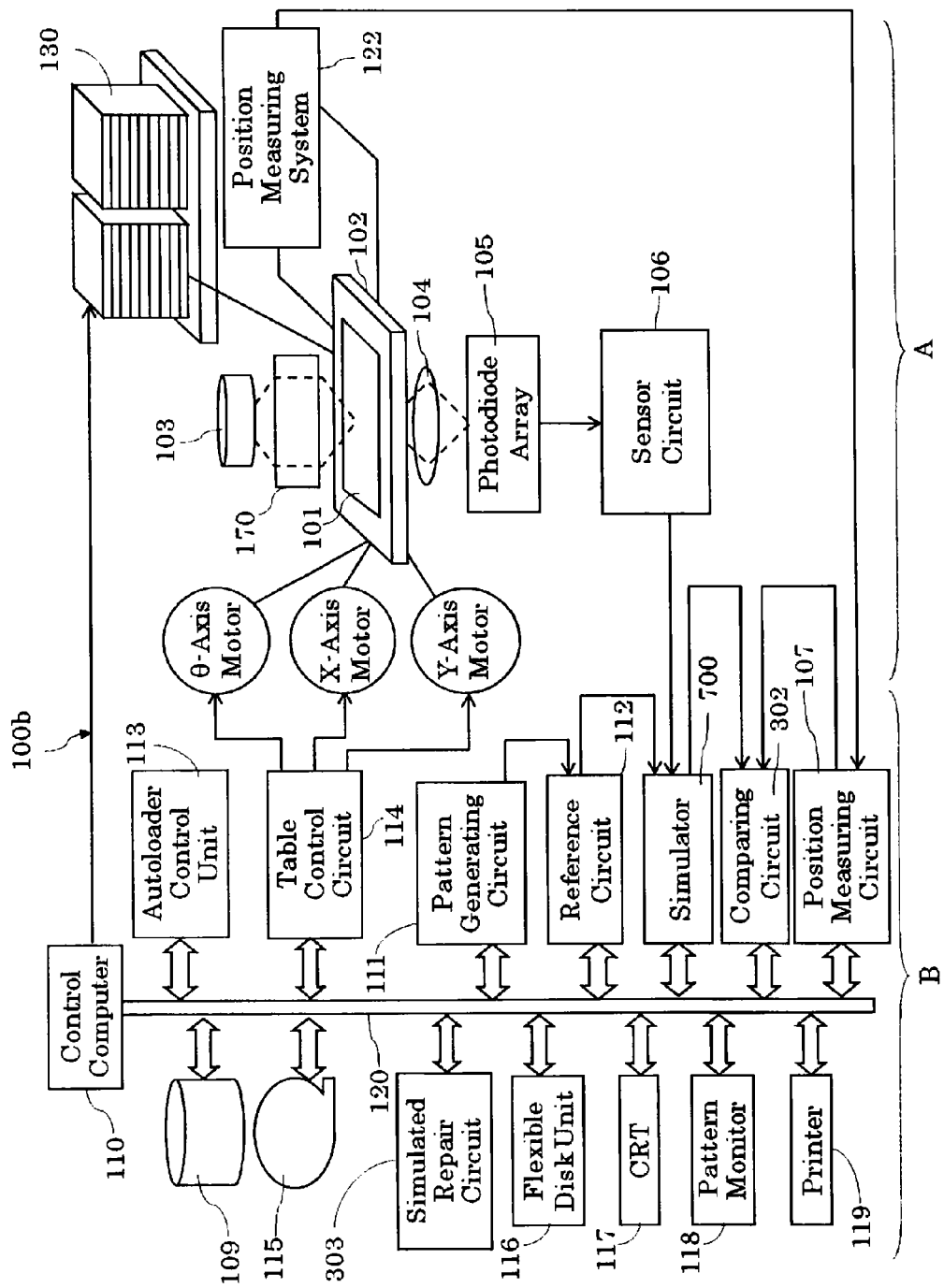
FIG. 15 is a diagram showing the configuration of an inspection system of Embodiment 2.

FIG. 15 is a diagram showing the configuration of this inspection system. The inspection system of the present Embodiment will be described in connection with the inspection of masks used in photolithography.

As shown in FIG. 15, the inspection system 100b includes an optical image capture unit A and a control unit B.

The optical image capture unit A includes alight source 103, an XYθ table 102 movable in the horizontal X and Y directions and rotatable in a horizontal plane (or in a θ direction), an optical illumination system 170 serving as a transmission illumination system, an enlarging optical system 104, a photodiode array 105, a sensor circuit 106, a position measuring system 122, and an autoloader 130.

In the control unit B, a control computer 110 which controls the entire inspection system 100b is connected through a bus 120 (serving as a data transmission path) to a position measuring circuit 107, a comparing circuit 302, a reference circuit 112, a pattern generating circuit 111, an autoloader control unit 113, a table control circuit 114, a storage unit 109 serving as a storage unit, a magnetic tape unit 115, a flexible disk unit 116, a CRT 117, a pattern monitor 118, and a printer 119. The XYθ table 102 is driven by X-, Y-, and θ-axis motors controlled by the table control circuit 114. These motors may be, e.g., step motors.

Design pattern data which is used as reference data in die-to-database inspection is stored in the storage unit 109. This data is read out and sent to the pattern generating circuit 111 when necessary in the course of the inspection process. The pattern generating circuit 111 converts the design pattern data into image data (or bit pattern data). This image data is then sent to the reference circuit 112 for generation of reference data.

It should be noted that the inspection system of the present Embodiment may include, in addition to the components shown in FIG. 15 described above, other known components required to inspect masks. Further, although the present Embodiment is described in connection with the die-to-database inspection method, it is to be understood that the Embodiment may be applied to the die-to-die inspection method. In such a case, an optical image of one of two separate identical patterns on the mask is treated as a reference image.

Figure 16:
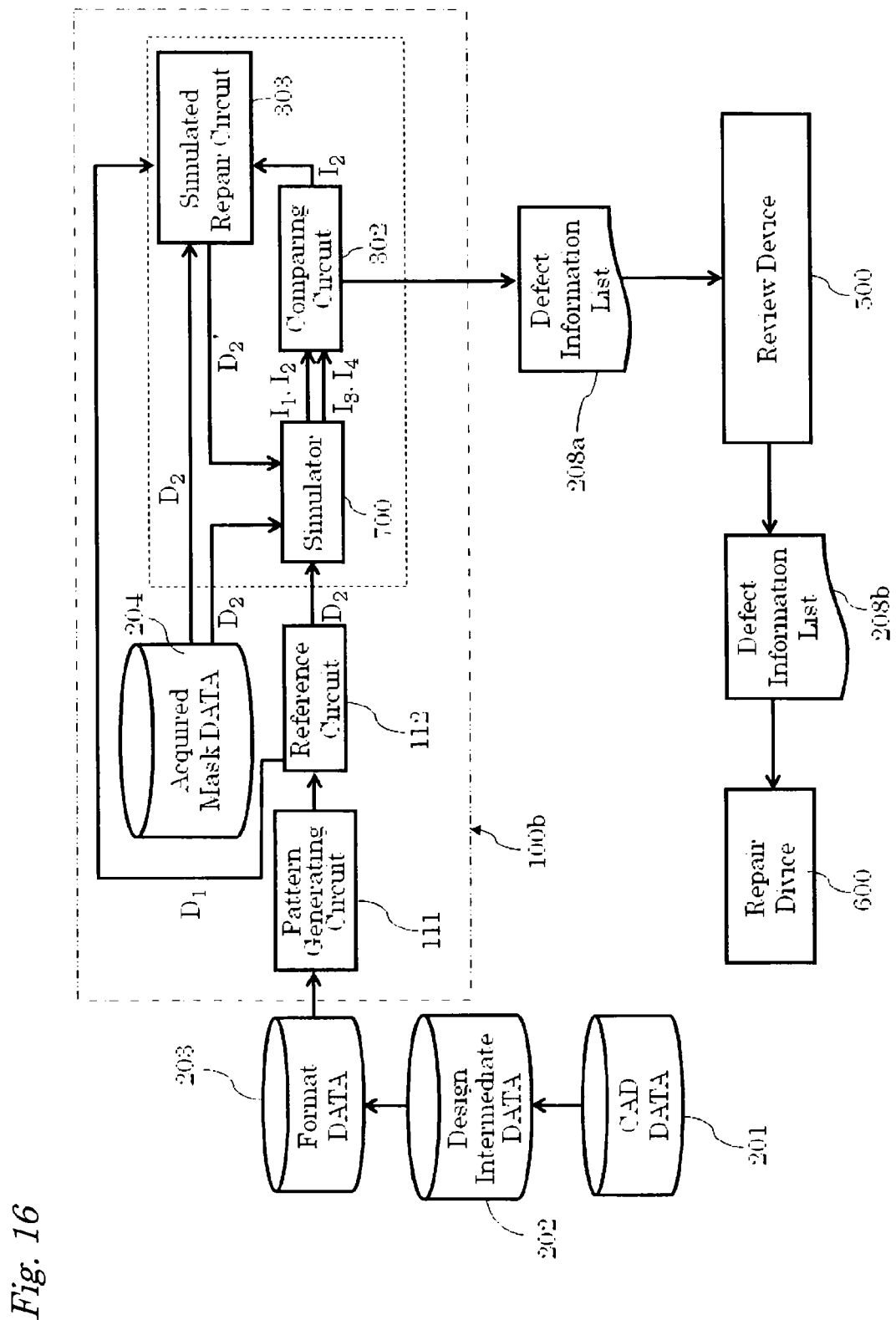
FIG. 16 is a schematic diagram showing a flow of data according to Embodiment 2.

FIG. 16 is a schematic diagram showing a flow of data according to the present Embodiment.

As shown in FIG. 16, CAD data 201 prepared by the designer (or user) is converted to design intermediate data 202 in a hierarchical format such as OASIS. The design intermediate data 202 includes data of the pattern formed on the mask created for each layer. It should be noted that, generally, writing apparatuses are not adapted to be able to directly read OASIS data. That is, each manufacturer of writing apparatus uses different format data. Therefore, OASIS data is converted, for each layer, to format data 203 in a format specific to the inspection system 100b used, and this format data 203 is input to the inspection system 100b. Although the format data 203 may be data inherent in the inspection system 100b, the format data 203 may also be data compatible with a drawing device.

The format data 203 is input to the storage unit 109 of FIG. 15. The design pattern data that was used to form the pattern on the photomask 101 is stored in the storage unit 109.

The designed pattern includes pattern features each consisting of basic features such as rectangles and triangles. The storage unit 109 stores feature data indicating the shape, size, and position of each pattern feature, specifically, e.g., information such as the coordinates (x, y) of the reference position of each feature, the length of its sides, and a shape code (or identifier) identifying the type of shape such as a rectangle or triangle.

Further, a group of pattern features defined in an area of approximately a few tens of micrometers square, is referred to as a "cluster" or "cell". It is common practice that the design pattern data is defined in a hierarchical structure using clusters or cells. A cluster (or cell), which contains a pattern feature or features, may be used alone or repeated at certain intervals. In the former case the coordinate positions of the cluster (or cell) on the photomask are specified, whereas in the latter case the coordinate positions of each copy of the cluster (or cell) are indicated together with a repetition instruction. Each cluster (or cell) is disposed in a strip-shaped region, referred to as a "frame" or "stripe", having a width of a few hundreds of micrometers and a length of approximately 100 mm which corresponds to the length of the photomask in the X or Y direction.

The pattern generating circuit 111 reads design pattern data of the photomask 101 from the storage unit 109 through the control computer 110.

Specifically, upon reading the design pattern data, the pattern generating circuit 111 generates data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

The design pattern data is converted into 2-bit or other multiple-bit image data (bit pattern data). This image data is sent to the reference circuit 112. After receiving the design image data (i.e., image data of the pattern), the reference circuit 112 performs appropriate filtering on the data.

FIG. 3 is a diagram illustrating the filtering.

The optical image i.e., acquired mask data 204 output from the sensor circuit 106 is somewhat "blurred" due to the resolution characteristics of the enlarging optical system 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image to be compared with the optical image is produced.

Next, a method of obtaining the mask data 204 will be described using FIGS. 15 and 4.

The optical image capture unit A shown in FIG. 15 captures mask data 204 of a photomask 101. It will be noted that this optical image (acquired mask data 204) includes an image of a pattern on the mask, this pattern was written in accordance with the corresponding design pattern data. The detailed method of capturing this optical image is as follows.

The photomask 101 serving as an inspection workpiece is mounted on the XYθ table 102 provided to be movable in two horizontal directions by X- and Y-axis motors and rotatable in a horizontal plane by a θ-axis motor. The pattern formed on the photomask 101 is then irradiated with light emitted from the light source 103 disposed above the XYθ table 102. More specifically, the beam of light emitted from the light source 103 passes through the optical illumination system 170 and shines on the photomask 101. The enlarging optical system 104, the photodiode array 105, and the sensor circuit 106 are disposed below the photomask 101. The light transmitted through the photomask 101 passes through the enlarging optical system 104 and reaches the photodiode array 105, thereby forming an optical image thereon. It should be noted that the enlarging optical system 104 may have its focus automatically adjusted by an autofocus mechanism (not shown). Further, though not shown, the inspection system 100*a* may be constructed such that light is also emitted from a source below the photomask 101, and the reflected light is passed through an enlarging optical system to a second photodiode array, thus capturing the transmitted light and the reflected light simultaneously.

FIG. 4 is a diagram illustrating the way in which mask data 204 is captured.

The inspection area is divided into a plurality of strip-shaped inspection stripes 20 by imaginary lines running in the X direction, where the width of each inspection stripe 20 in the Y direction is equal to the scan width W, as shown in FIG. 4. The movement of the XYθ table 102 is controlled so that each inspection stripe 20 is continuously scanned in the negative or positive X direction with the light to capture an image of the inspection stripe. At that time, the photodiode array 105 continuously generates an image (of each inspection stripe 20) having a width corresponding to the scan width W, as shown in FIG. 4. After capturing an image of the first inspection stripe 20 by scanning it, e.g., in the negative X direction, the second inspection stripe 20 is continuously scanned in the positive (i.e., opposite) X direction to capture an image of a width corresponding to the scan width W. Likewise, the third inspection stripe 20 is scanned in the negative x direction (opposite the direction in which the second inspection stripe 20 is scanned) to capture an image. This way of continuously capturing an image of one inspection stripe 20 after another reduces waste of processing time.

The pattern image formed on the photodiode array 105 as shown in FIG. 15 is photoelectrically converted by the array 105 and A/D (analog to digital) converted by the sensor circuit 106. The photodiode array 105 is made up of sensors arranged in an array. These sensors may be, for example, TDI (Time Delay Integration) sensors. Thus, the pattern on the photomask 101 is imaged by these TDI sensors while the XYθ table 102 is continuously moved in the positive or negative X direction. It will be noted that the light source 103, the enlarging optical system 104, the photodiode array 105, and the sensor circuit 106 together form a high power optical inspection system.

The XYθ table 102 can be moved in the X and Y directions and rotated in a θ direction (or in an XY plane) by a drive system such as a 3-axis (X-Y-θ) motor driven by the table control circuit 114 under the control of the control computer 110. These X-, Y-, and θ-axis motors may be, e.g., step motors. The position of the XYθ table 102 is measured by the position measuring system 122, and the measurement data is sent to the position measuring circuit 107. Further, the photomask 101 is automatically loaded onto the XYθ table 102 from the autoloader 130 driven by the autoloader control unit 113, and, upon completion of its inspection, the photomask 101 is automatically retrieved from the XYθ table 102.

As shown in FIGS. 15 and 16, the optical image data $D_2$ output from the sensor circuit 106 is sent to the simulator 700. The reference image data $D_1$ generated in the reference circuit 112 is also sent to the simulator 700. A portion surrounded by a dot line in FIG. 16 is a portion having the defect estimation function described in the first aspect.

The simulator 700 estimates a pattern image to be transferred from the mask to the wafer, using the reference image data $D_1$ and the optical image data $D_2$. The pattern image may be a resist pattern image at any stage in a series of a lithography process such as development and etching or may be a circuit pattern image finally formed in the wafer. The wafer is an example of a substrate in this invention.

For example, a photo mask formed with a predetermined circuit pattern is a test object. The photo mask is used for transferring the circuit pattern onto a wafer. The transfer is performed by the following process, for example. First, a resist film is provided on the wafer. Next, the wafer is exposed by an exposure device through the photo mask to transfer an exposure image of the circuit pattern to the resist film. Then, the resist film is developed to form a resist pattern. Thereafter, a lower film is etched using the resist pattern as a mask, and after that, the resist film is peeled. Consequently, the lower film can be processed to a pattern having a desired shape. Next, copper (Cu) or the like is filled in a recess of the lower film, and thereafter, an unnecessary portion is removed by a CMP (Chemical Mechanical Planarization) method, whereby a wiring pattern is formed.

In the above example, the simulator 700 can estimate the exposure image to be transferred from the mask to the wafer by the exposure device, for example, and can also estimate a resist pattern image to be formed on the wafer. Alternatively, the simulator 700 can estimate a pattern image of the recess to be formed in the lower film and a wiring pattern image after having been filled with copper and the like. These pattern images include a pattern image $I_1$ estimated from the reference image data $D_1$ and a pattern image $I_2$ estimated from the optical image data $D_2$. In the present Embodiment, images estimated by the simulator 700, that is, the exposure image transferred from the mask to the wafer by the exposure image, the resist pattern image formed on the wafer, the wiring pattern image, and so on are collectively referred to as pattern images and are estimated from the reference image data $D_1$ and the optical image data $D_2$.

The pattern images $I_1$ and $I_2$ estimated by the simulator 700 are sent to the comparing circuit 302 along with data output from the position measuring circuit 107 showing the position of the photomask 101 on the XYθ table 102.

In the comparing circuit 302, the pattern image $I_1$ estimated from the reference image data $D_1$ and the pattern image $I_2$ estimated from the optical image data $D_2$ are compared with each other using the appropriate comparative determination algorithm. For example, when a defect after etching is estimated, the information of the patterns after etching to be described respectively in the pattern images $I_1$ and $I_2$ are compared, and when the difference between the positions of the corresponding sides is more than a predetermined level, for example, 4 nm, it is regarded that there is a defect. As the result of the comparison, when it is determined that there is a defect, the coordinate and the pattern images $I_1$ and $I_2$ as the basis for the defect determination are stored in the comparing circuit 302.

With regard to the portion determined as a defect based on the pattern images $I_1$ and $I_2$, the reference image data $D_1$ of the mask at the corresponding position and the optical image data $D_2$ are sent to the simulated repair circuit 303. In the simulated repair circuit 303, simulated repair is applied to the defect portion sent to the simulated repair circuit 303. The simulated repair is performed as follows. The reference image data $D_1$ of the mask and the optical image data $D_2$ are compared with each other, and different positions are found around the position estimated as a defect. The optical information at the different position is replaced with the corresponding optical information of the optical image data $D_2$. For example, the information of the defect portion denoted by the reference numeral 10 in FIG. 9*a* is replaced with the information of the defect portion denoted by the reference numerals 701 and 702 in FIG. 7*b*. At that time, when there are a plurality of defects in the pattern image $I_2$, a plurality of times of simulated repair are performed changing the repaired portion.

For example, if the repair of a defect portion can restore the wafer transfer image to a normal state, then in the repair process we should only be concerned with this specific portion. On the other hand, if an individual defect portion is repaired but the wafer optical image cannot be restored to a normal state then a combination of two portions is to be repaired. If any of the above combinations do not restore the wafer transfer image to a normal state then a combination of three portions are repaired. Furthermore, any combination of portions exceeding this number can be utilized in any combination to restore the wafer transfer image to its normal state.

When contiguous defect coordinates are stored as optical image data $D_2$ in the comparing circuit 302, in the simulated repair circuit 303, simulated repair is performed for each region including the defects. That is to say, the repair to the optical image data $D_2$ including all defects in a predetermined range is simulated.

The simulated optical image data $D_2$ as new optical image data $D_2'$ is returned to the simulator 700 again. In the simulator 700, a new pattern image $I_3$ is estimated from the reference image data $D_1$ as a model, and a new pattern image $I_4$ is also estimated from the simulated optical image data $D_2'$. When a plurality of times of simulated repair are performed changing the defect portion to be repaired, a plurality of the new pattern images $I_4$ estimated from the repaired optical image data $D_2'$ are obtained.

The pattern images $I_3$ and $I_4$ may be at the same stage of the lithography process as the pattern image $I_1$ and $I_2$ or may be in the more advanced state than the pattern image $I_1$ and $I_2$. For example, all the pattern images $I_1$, $I_2$, $I_3$ and $I_4$ may be exposure images transferred from the mask to the wafer by the exposure device. When the pattern images $I_1$ and $I_2$ are resist pattern images formed on the wafer, the pattern images $I_3$ and $I_4$ may be wiring pattern images formed on the wafer.

The pattern images $I_3$ and $I_4$ newly estimated by the simulator 700 are sent from the simulator 700 to the comparing circuit 302 again. The pattern image $I_3$ as a model and the pattern image $I_4$ after simulated repair are compared with each other, whereby confirmation can be made as to whether or not the initially indicated defect on the wafer is eliminated. As the result of the comparison, the coordinate determined as a defect and the pattern images $I_3$ and $I_4$ as the basis for the defect determination are sent as the defect information list 208*a* to the review device 500, which is an external device of the inspection device, along with the reference image data $D_1$ and the optical image data $D_2$.

All defects detected by the inspection device 100*b* are discriminated in the review device 500. However, when the defect detected in the wafer transfer image is minor, the defect may be removed from an object to be reviewed by pre-processing.

In this review process, the operator determines whether a pattern defect found in the inspection can be tolerated. In the review device 500, an image at the defect portion of the mask is displayed while a table on which the mask is placed is moved so that the defect coordinates of defects can be observed one by one. At the same time, the judgment of the defect determination, the optical image as a basis for the determination and the reference image are arranged and displayed on a screen so that the determined condition, the optical image and the reference image can be confirmed. The defect on the mask and the influence on the wafer transfer image are arranged and displayed in a review process, whereby the determination whether or not the mask pattern should be repaired is facilitated. In general, projection from the mask to the wafer is performed while reduction to approximately quarter size is performed, and therefore, when images are arranged and displayed, the reduction scale is considered.

The discriminated defect information is returned to the inspection system 100*b* and stored in the storage unit 109. When even one defect to be repaired is confirmed in the review device 500, the mask is sent to a repair device 600, which is an external device of the inspection system 100*a*, along with a defect information list 208*b*. Since the repair method is different according to the type of the defect, that is, between the extrusion and intrusion defects, the type of the defect including discrimination between the extrusion and intrusion defects and the coordinate of the defect are added to the defect information list 208*b*.

In a second aspect of the second Embodiment, the inspection system 100*b* itself may have the review function. In this case, the mask inspection results 205 and the transfer image inspection results 206 are displayed as images with incidental information of the defect determination on the screen of the control Computer 110 or a screen of a separately provided calculator. The image of the mask defect portion is displayed using an optical observation system image of the inspection system 100*a*.

As described above, in the inspection device according to the second aspect of Embodiment 2, the pattern image after being transferred from the optical image to the wafer is estimated to be compared with the pattern image estimated from the reference image in a similar manner, whereby the presence of a defect is determined. After the simulated repair of the pattern image at the portion determined as a defect, the pattern image is compared with the image as a model again, and the presence of defect is determined. As a result, the defect on the mask, the influence of the defect on the wafer, and the degree of the improvement by the repair can be estimated. Accordingly, according to the inspection system and the inspection method of the present Embodiment, the degree of influence of the mask defect on the wafer and the portion of the pattern on the mask to be repaired for eliminating the detected defect can be determined.

The inspection system in the second aspect of Embodiment 2 is not limited to the above-mentioned example as shown in FIG. 15 and may be repaired without departing from the spirit and scope of the present invention.

In this case, Unit A of the optical image data apparatus as shown in FIG. 15 can utilize an irradiating laser beam light source 103. However, optical image data can also be acquired using an electron beam. For example, the inspection apparatus can use SEM (Scanning Electron Microscope) or MEM (Mirror Electron Microscope).

Figure 22:
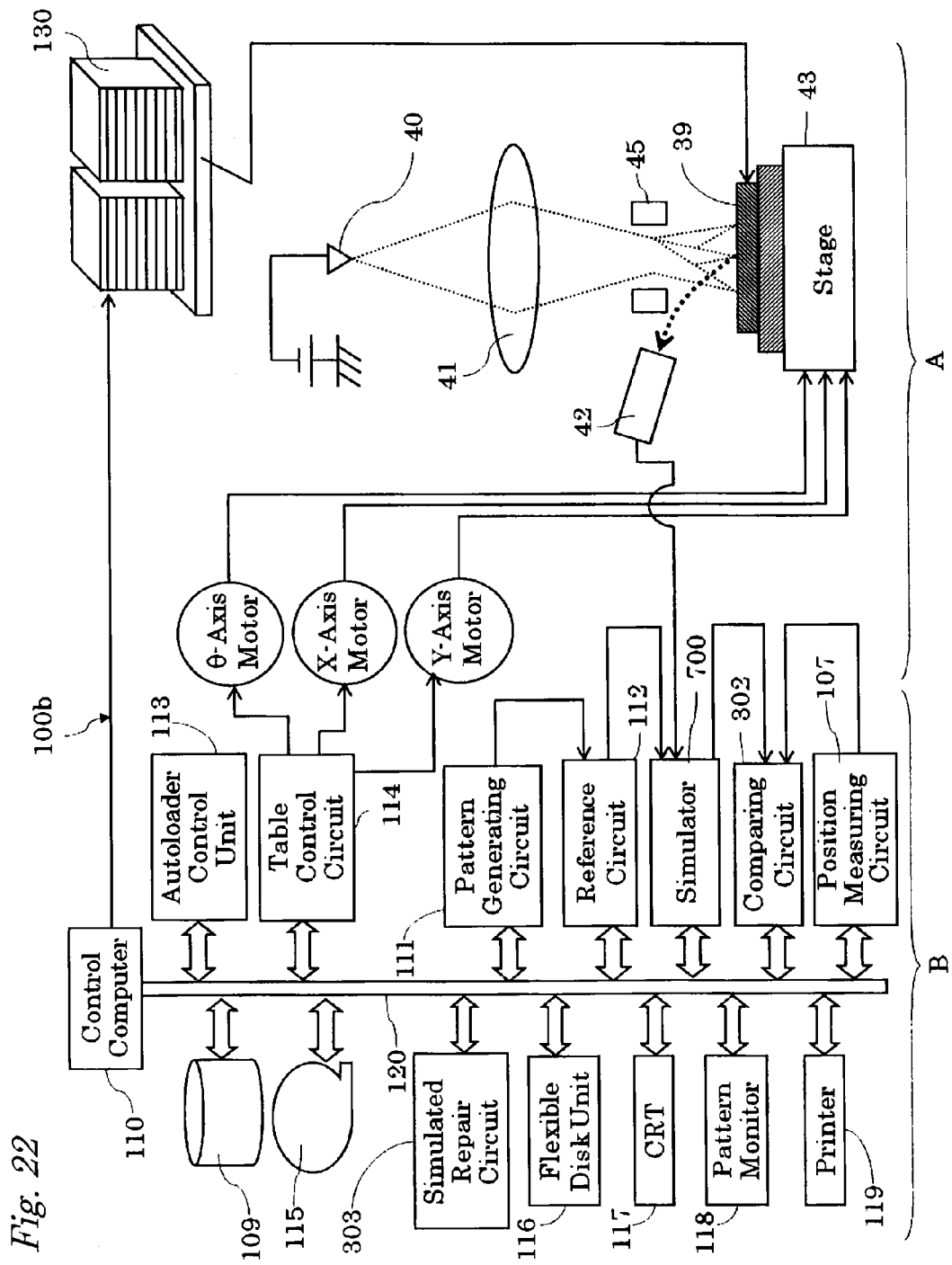
FIG. 22 is an example of optical image data acquisition using SEM (Scanning Electron Microscope) according to Embodiment 2.

The inspection apparatus as shown in FIG. 22 is an example of an inspection apparatus utilizing SEM technique. The individual component numbers are the same as for FIG. 15 with the exception of Unit A.

In the example of FIG. 22 the electron beam from the electron gun 40 is focused by the condenser lens 41 and then irradiated to the mask 39 placed on the stage 43. The movement of the scanning line and scanning speed on the mask 39 are controlled by the scanning coil 45. After the electron beam is irradiated on the mask 39 the reflected electron beam is guided to the detector 42. The output signal from the detector 42 is amplified by the sensor (not shown), then converted to digital data, this signal is then sent to the simulator 700.

Figure 23:
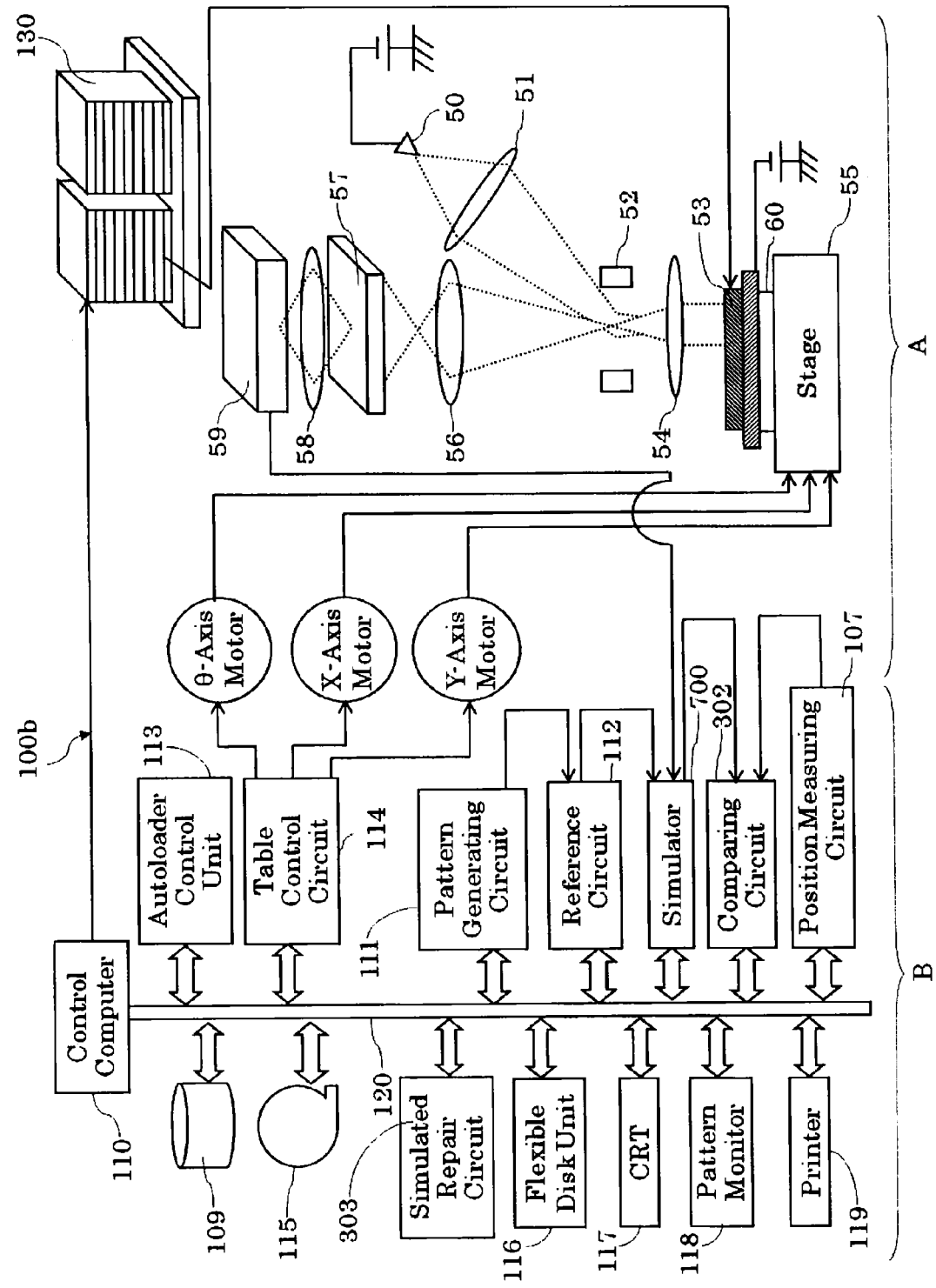
FIG. 23 is an example of optical image data acquisition using MEM (Mirror Electron Microscope) according to Embodiment 2.

FIG. 23 is another example using MEM to acquire optical image data as in unit A of FIG. 15. The individual component numbers are the same as in FIG. 15 with the exception of Unit A.

In FIG. 23 the mask 53 is placed on an insulated material 60 on the stage 55. The electron beam from the electron beam gun 50 is focused by the condenser lens 51, then deflected by the ExB deflector 52, after, the electron beam passes through the objective lens 54 forming an expanded beam which reaches the mask 53 vertically. After the electron beam is irradiated on the mask 53 the reflected beam is transmitted through the objective lens 54 to the focus lens 56 and is then projected on to the fluorescent screen 57. The optical image on the fluorescent screen 57 is focused on the received light plate of CCD 59 by an optical lens 58. Then, the image of pattern focused on the CCD 59 is transformed to digital data and sent to the simulator 700.

(3) Defect Estimation Device and Defect Estimation Method

A defect estimation device and a defect estimation method according to a third aspect of the Embodiment 2 will be described with reference to FIG. 17. A portion surrounded by a dot line in FIG. 13 is a main portion constituting the defect estimation device.

The defect estimation device has a first simulator 401, a first comparing circuit 402, a simulated repair circuit 403, a second simulator 404, and a second comparing circuit 405. The first simulator 401 estimates a first pattern image, and the second simulator 404 estimates a second pattern image. In the second pattern image, the lithography process is more advanced than that in the first pattern image. That is to say, since only the simulator 700 is provided in the Embodiment 1, calculation processing performed before and after the simulated repair is basically the same. On the other hand, in the present Embodiment, since two simulators are provided, the present Embodiment is characterized in that the processing methods are different.

The reference image data $D_1$ and the optical image data $D_2$ are input to the first simulator 401. This data can be generated in the inspection device as described in the Embodiment 2.

The first simulator 401 estimates first pattern images $I_5$ and $I_6$ using the input reference image data $D_1$ and optical image data $D_2$.

For example, a photo mask formed with a predetermined circuit pattern is a test object. The photo mask is used for transferring the circuit pattern onto a wafer. The transfer is performed by the following process, for example. First, a resist film is provided on the wafer. Next, the wafer is exposed by an exposure device through the photo mask to transfer an exposure image of the circuit pattern to the resist film. Then, the resist film is developed to form a resist pattern. Thereafter, a lower film is etched using the resist pattern as a mask, and after that, the resist film is peeled. Consequently, the lower film can be processed to a pattern having a desired shape. Next, copper (Cu) or the like is filled in a recess of the lower film, and thereafter, an unnecessary portion is removed by a CMP (Chemical Mechanical Planarization) method, whereby a wiring pattern is formed.

In the above example, the first simulator 401 can estimate the exposure image of a wiring pattern image to be transferred on to the wafer, for example, these exposure images include a pattern image $I_5$ estimated from the reference image data $D_1$ and a pattern image $I_6$ estimated from the optical image data $D_2$.

The first pattern images $I_5$ and $I_6$ estimated by the first simulator 401 are sent to the first comparing circuit 402. In the first comparing circuit 402, the pattern image $I_5$ as a model estimated from the reference image data $D_1$ and the pattern image $I_6$ estimated from the optical image data $D_2$ are compared with each other using the appropriate comparative determination algorithm. For example, in a pattern after CMP processing, the simulation of CMP itself is similar to that in the example of etching, and the information described respectively in obtained pattern images are compared. When the difference between the positions of the corresponding sides is more than a predetermined level, for example, 4 nm, it is regarded that there is a defect. As the result of the comparison, when it is determined that there is a defect, the coordinate and the first pattern images $I_5$ and $I_6$ as the basis for the defect determination are stored in the first comparing circuit 402.

With regard to the portion determined as a defect based on the first pattern images $I_5$ and $I_6$, the reference image data $D_1$ of the mask at the corresponding position and the optical image data $D_2$ are sent from the first comparing circuit 402 to the simulated repair circuit 403. In the simulated repair circuit 403, simulated repair is applied to the defect portion sent to the simulated repair circuit 403. The simulated repair is performed as follows. The reference image data $D_1$ of the mask and the optical image data $D_2$ of the mask are compared, and different positions are found around the position estimated as a defect. The optical information at the different position is replaced with the corresponding optical information of the reference image. For example, the information of the defect portion denoted by the reference numeral 10 in FIG. 9a is replaced with the information of the defect portion denoted by the reference numerals 701 and 702 in FIG. 7b. When there are a plurality of defects in the pattern image $I_6$, the repaired portion is changed, and a plurality of times of simulated repair are performed while changing the repaired portion, whereby a defect that will cause a pattern error can be specified.

For example, if the repair of a defect portion can restore the wafer transfer image to a normal state, then in the repair process we should only be concerned with this specific portion. On the other hand, if an individual defect portion is repaired but the wafer optical image cannot be restored to a normal state then a combination of two portions is to be repaired. If any of the above combinations do not restore the wafer transfer image to a normal state then a combination of three portions are repaired. Furthermore, any combination of portions exceeding this number can be utilized in any combination to restore the wafer transfer image to its normal state.

When contiguous defect coordinates as optical image data $D_2$ are stored in the first comparing circuit 402, in the simulated repair circuit 403, simulated repair is performed for each region including the defects. That is to say, the repair of the optical image data $D_2$ including all defects in a predetermined range is simulated. In a pattern established by a combination of a plurality of patterns, the constituent patterns influence each other to be transferred as one pattern on a wafer. Thus, also when repair of a simulated pattern image is estimated, repair of the mutual influence between a plurality of defect portions should be considered. This is because, when the pattern image is estimated for each defect, a real pattern image is not estimated.

The simulated optical image data $D_2$ is sent as the optical image data $D_2'$ to the second simulator 404. In the second simulator 404, a second pattern image $I_7$ is newly estimated from the reference image data $D_1$ as a model, and a second pattern image $I_8$ is also estimated from the optical image data $D_2'$. When a plurality of times of simulated repair are performed changing the defect portion to be repaired, a plurality of the second pattern images $I_8$ estimated from the repaired optical image data $D_2'$ are obtained.

The second pattern images $I_7$ and $I_8$ are in the more advanced state than the first pattern images $I_5$ and $I_6$. For example, when the first pattern images $I_5$ and $I_6$ are exposure images of a circuit pattern transferred onto a wafer, the second pattern images $I_7$ and $I_8$ may be resist pattern images at any stage in a series of a lithography process such as development and etching or may be circuit pattern images finally formed in a wafer. The circuit pattern may be any of circuit patterns before and after the CMP processing.

A specific stage of the second pattern images $I_7$ and $I_8$ in the lithography process can be suitably selected according to the process.

For example, in the etching processing of a wiring material using a resist pattern as a mask, dimensional variation due to a microloading effect may occur. The dimensional variation increases as a density difference in of a circuit pattern increases. This is because there is a variation between a region where a circuit pattern to be formed on a wafer is dense and a region where the circuit pattern is sparse, a larger number of active species required for etching are inhibited in a region where the circuit pattern is sparse, whereas less active species are required if the circuit pattern is dense. Therefore, a circuit pattern having a desired dimension (determined by pattern data as a basis) cannot be obtained. That is to say, in the region where a circuit pattern to be formed on the wafer is sparse, the dimension of the pattern formed by etching is larger than a desired pattern dimension. Meanwhile, in the region where the circuit pattern to be formed on the wafer is dense, the dimension of the pattern formed by etching is smaller than the desired pattern dimension.

To solve the above problem, a correction processing for pattern data is performed over all minute sections in the circuit pattern. Consequently, although the pattern dimension after development processing deviates from a desired dimension, the pattern after etching has a desired dimension. Thus, in this example, if the second pattern image estimated by the second simulator 404 is a resist pattern image after development, all patterns may be possibly judged as defects. However, if the second pattern image is a resist pattern image after etching or a wiring pattern image, the presence of a defect can be accurately determined.

The second pattern images $I_7$ and $I_8$ estimated by the second simulator 404 are sent to the second comparing circuit 405. In the second comparing circuit 405, the second pattern image $I_7$ as a model and the second pattern image $I_8$ estimated from the optical image data $D_2'$ after simulated repair are compared with each other, whereby confirmation can be made as to whether or not the initially indicated defect on the wafer is eliminated. As the result of the comparison, the coordinate determined as a defect and the second pattern images $I_7$ and $I_8$ as the basis for the defect determination are output as a defect information list 209 to an external device along with the reference image data $D_1$ and the optical image data $D_2$.

The second comparing circuit 405 may not be provided in the defect estimation device according to the third aspect of the Embodiment 2. In this case, the defect estimation device outputs the second pattern images $I_7$ and $I_8$ estimated by the second simulator 404, the reference image data $D_1$, and the optical image data $D_2$ to an external device. When the external device is an inspection device, the inspection device receives the above data from the defect estimation device and, in the internal comparing circuit, compares the second pattern image $I_7$ as a model with the second pattern image $I_8$ estimated from the optical image data $D_2'$ after simulated repair. As a result, it can be confirmed whether or not the initially indicated defect on the wafer is eliminated in the defect estimation device.

Figure 17:
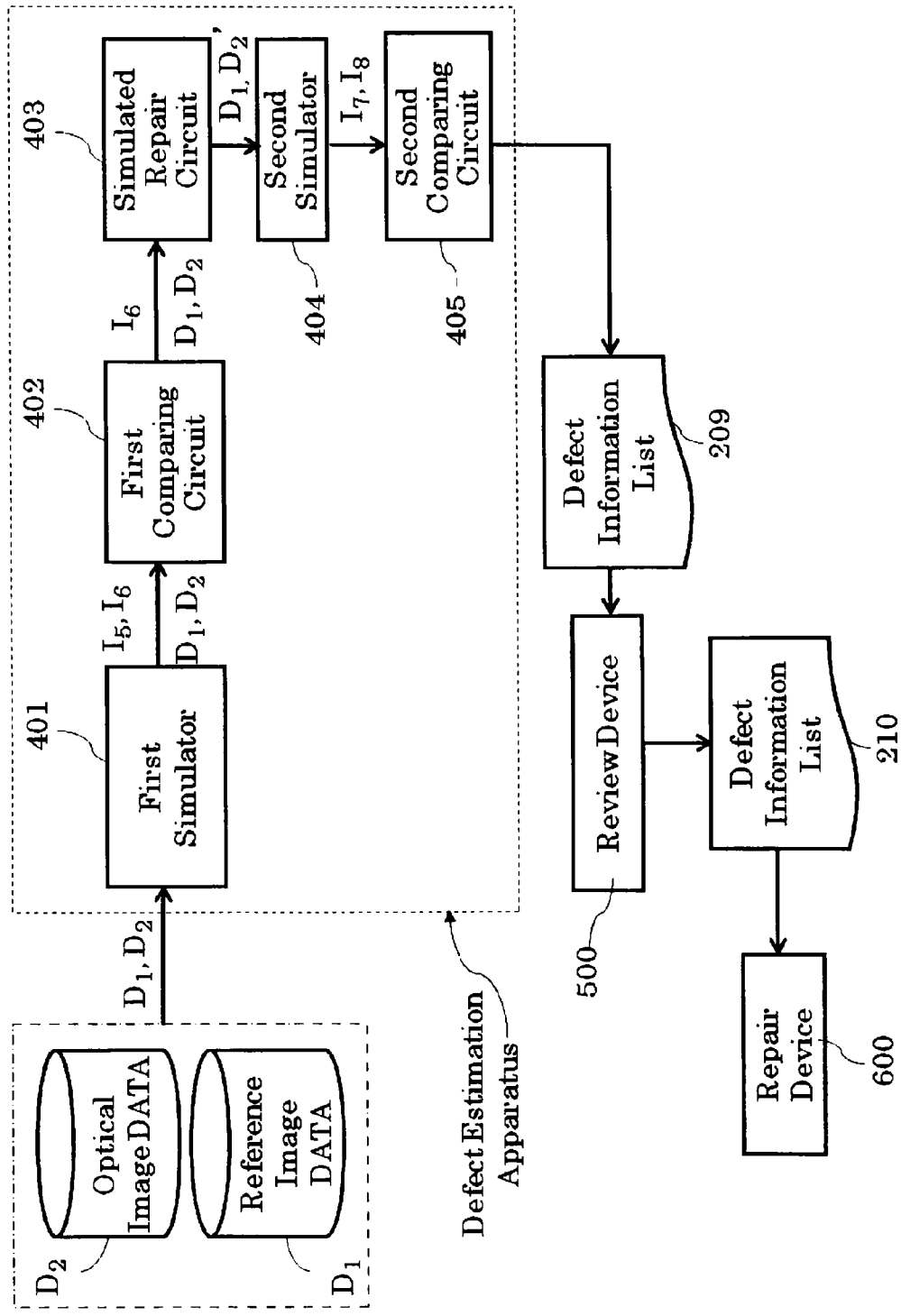
FIG. 17 shows a defect estimation device and a defect estimation method according to a third aspect of the Embodiment 2.

As shown in FIG. 17, the defect information list 209 is sent to the review device 500. In the review device 500, an image at the defect portion of the mask is displayed while a table on which the mask is placed is moved so that the defect coordinates of defects can be observed one by one. At the same time, the condition of the defect determination, second pattern image $I_7$ and $I_8$, reference image data $D_1$ and optical image data $D_2$ as a basis for the determination, are arranged and displayed on a screen so that the judgment, the optical image and the reference image can be confirmed. The defect on the mask and the influence on the wafer transfer image are arranged and displayed in a review process, whereby the determination whether or not the mask pattern should be repaired is facilitated. In general, projection from the mask to the wafer is performed while reduction to approximately quarter size is performed, and therefore, when images are arranged and displayed, the reduction scale is considered.

When even one defect to be repaired is confirmed in the review device 500, the mask is sent to a repair device 600, which is an external device of the inspection system 100a, along with a defect information list 208b. Since the repair method is different according to the type of the defect, that is, between the extrusion and intrusion defects, the type of the defect including discrimination between the extrusion and intrusion defects and the coordinate of the defect are added to the defect information list 208b.

As described above, in the defect estimation device and the defect estimation method in the third aspect of Embodiment 2, the pattern image after being transferred from the optical image to the wafer is estimated to be compared with the pattern image estimated from the reference image in a similar manner, whereby the presence of defect is determined. After the simulated repair of the pattern image at the portion determined as a defect, the pattern image is compared with the image as a model again, and the presence of defect is determined. As a result, the defect on the mask, the influence of the defect on the wafer, and the degree of the improvement by the repair can be estimated.

Since the initial simulation is performed simply, the entire calculation processing can be increased in speed.

In the defect estimation device and the defect estimation method in the third aspect of the Embodiment 2, although the reference image is a standard image, it is not limited thereto. That is to say, the standard image may be a reference image created from design data of a pattern or an optical image having the same pattern in a region different from the optical image which is an object on a mask.

(2) Inspection System

An inspection device according to a fourth aspect of the Embodiment 2 is characterized by including the function of the defect estimation device according to the third aspect.

Figure 18:
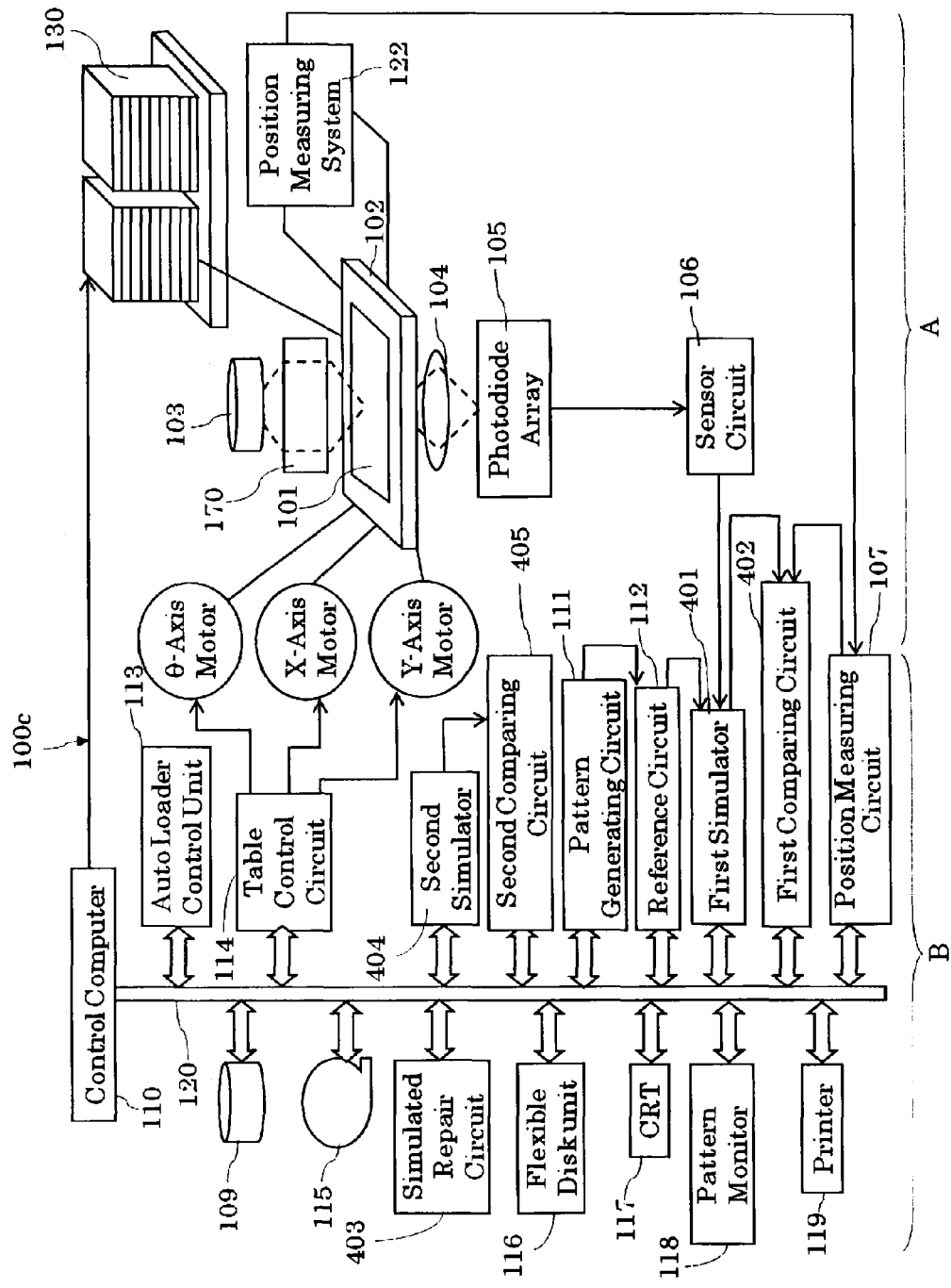
FIG. 18 is a diagram showing the configuration of this inspection system according to the fourth aspect of Embodiment 2.

FIG. 18 is a diagram showing the configuration of this inspection system according to the fourth aspect of Embodiment 2. As shown in FIG. 18, inspection system 100c has an optical image capture unit A and a control unit B. In FIG. 18, the same components as those in FIG. 15 are denoted by the same reference numerals, and therefore, the description will not be repeated here. It should be noted that the inspection system of the present Embodiment may include, in addition to the components shown in FIG. 18 described above, other known components required to inspect masks. Further, although the present Embodiment is described in connection with the die-to-database inspection method, it is to be understood that the Embodiment may be applied to the die-to-die inspection method. In such a case, an optical image of one of two separate identical patterns on the mask is treated as a reference image.

Figure 19:
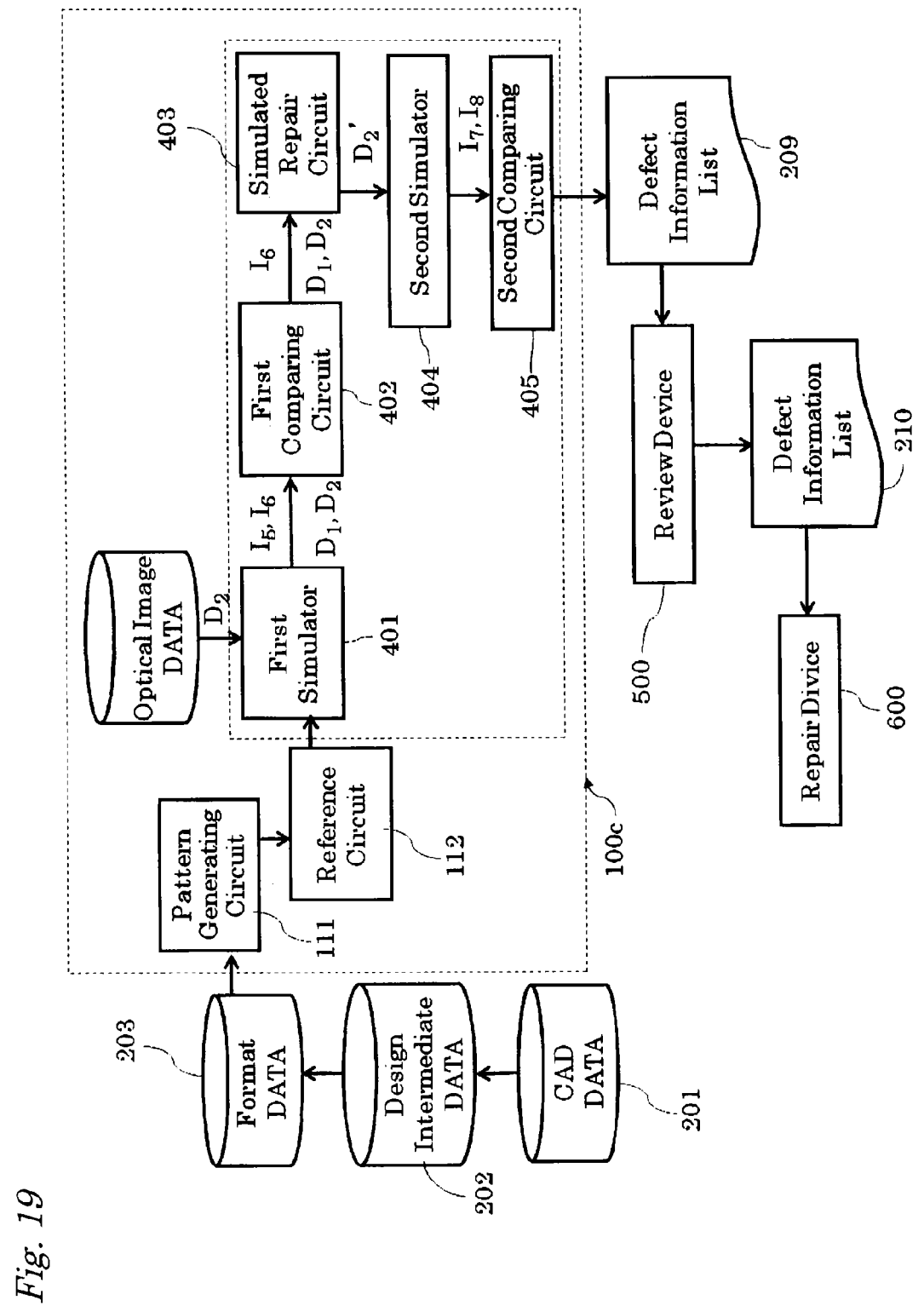
FIG. 19 is a schematic diagram showing a flow of data according to Embodiment 2.

FIG. 19 is a schematic diagram showing a flow of data according to the present Embodiment.

As shown in FIG. 19, CAD data 201 prepared by the designer (or user) is converted to design intermediate data 202 in a hierarchical format such as OASIS. The design intermediate data 202 includes data of the pattern formed on the mask created for each layer. It should be noted that, generally, writing apparatuses are not adapted to be able to directly read OASIS data. That is, each manufacturer of writing apparatus uses different format data. Therefore, OASIS data is converted, for each layer, to format data 203 in a format specific to the inspection system 100c used, and this format data 203 is input to the inspection system 100c. Although the format data 203 may be data inherent in the inspection system 100c, the format data 203 may also be data compatible with a drawing device.

The format data 203 is input to the storage unit 109 of FIG. 18. The pattern generating circuit 111 reads the format data 203 from the storage unit 109 through the control computer 110.

Specifically, upon reading the design pattern data, the pattern generating circuit 111 generates data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

The design pattern data is converted into 2-bit or other multiple-bit image data (bit pattern data). This image data is sent to the reference circuit 112. After receiving the design image data (i.e., image data of the pattern), the reference circuit 112 performs appropriate filtering on the data.

As shown in FIGS. 18 and 19, the optical image data $D_2$ output from the sensor circuit 106 is sent to the first simulator 401. The reference image data $D_1$ generated in the reference circuit 112 is also sent to the first simulator 401. A portion surrounded by a dot line in FIG. 19 is a portion having the defect estimation function described in the Embodiment 3.

The first simulator 401 estimates a first pattern image using the reference image data $D_1$ and the optical image data $D_2$.

For example, a photo mask formed with a predetermined circuit pattern is a test object. The photo mask is used for transferring a pattern onto a wafer. The transfer is performed by the following process, for example. First, a resist film is provided on the wafer. Next, the wafer is exposed by an exposure device through the photo mask to transfer an exposure image of the circuit pattern to the resist film. Then, the resist film is developed to form a resist pattern. Thereafter, a lower film is etched using the resist pattern as a mask, and after that, the resist film is peeled. Consequently, the lower film can be processed to a pattern having a desired shape. Next, copper (Cu) or the like is filled in a recess of the lower film, and thereafter, an unnecessary portion is removed by a CMP (Chemical Mechanical Planarization) method, whereby a wiring pattern is formed.

In the above example, the first simulator 401 can estimate an exposure image of a circuit pattern transferred as a first pattern image onto a wafer. The pattern image includes the pattern image $I_5$ estimated from the reference image data $D_1$ and the pattern image $I_6$ estimated from the optical image data $D_2$.

The first pattern images $I_5$ and $I_6$ estimated by the first simulator 401 are sent to the first comparing circuit 402. In the first comparing circuit 402, the first pattern image $I_5$ as a model estimated from the reference image data $D_1$ and the first pattern image $I_6$ estimated from the optical image data $D_2$ are compared with each other using the appropriate comparative determination algorithm. For example, when a resist pattern after etching is estimated as the first pattern image, the information of the patterns described respectively in the first pattern images $I_5$ and $I_6$ obtained in the simulation are compared. When the difference between the positions of the corresponding sides is more than a predetermined level, for example, 4 nm, it is regarded that there is a defect. As the result of the comparison, when it is determined that the defect occurs, the coordinate and the first pattern images $I_5$ and $I_6$ as the basis for the defect determination are stored in the first comparing circuit 402.

With regard to the portion determined as a defect based on the first pattern images $I_5$ and $I_6$, the reference image data $D_1$ of the corresponding mask and the optical image data $D_2$ are sent to the simulated repair circuit 403. In the simulated repair circuit 403, simulated repair is applied to the defect portion sent to the simulated repair circuit 403. The simulated repair is performed as follows. The reference image data $D_1$ and the optical image data $D_2$ are compared, and different positions are found around the position estimated as a defect. The optical information at the different position is replaced with the corresponding optical information of the reference image data $D_1$. For example, the information denoted by the reference numeral 10 in FIG. 9a is replaced with the information indicated by the reference numerals 701 and 702 in FIG. 7b. At that time, when there are a plurality of defects in the first pattern image $I_6$, the repaired portion is changed, and a plurality of times of simulated repair are performed.

For example, if the repair of a defect portion can restore the wafer transfer image to a normal state, then in the repair process we should only be concerned with this specific portion. On the other hand, if an individual defect portion is repaired but the wafer optical image cannot be restored to a normal state then a combination of two portions is to be repaired. If any of the above combinations do not restore the wafer transfer image to a normal state then a combination of three portions are repaired. Furthermore, any combination of portions exceeding this number can be utilized in any combination to restore the wafer transfer image to its normal state.

When contiguous defect coordinates as the different first pattern image $I_6$ are stored in the first comparing circuit 402, in the simulated repair circuit 403, simulated repair is performed for each region including the defects. That is to say, repair to the different first pattern image $I_6$ including all defects in a predetermined range is simulated. In a pattern established by a combination of a plurality of patterns, the constituent patterns influence each other to be transferred as one pattern on a wafer. Thus, also when a repair of a simulated pattern image is estimated, the mutual influence between a plurality of defect portions should be considered. This is because, when the pattern image is estimated for each defect, a real pattern image is not estimated.

The simulated repair of optical image data $D_2$ is sent as the optical image data $D_2'$ to the second simulator 404. In the second simulator 404, a second pattern image $I_7$ is newly estimated from the reference image data $D_1$ as a model, and a second pattern image $I_8$ is also estimated from the simulated optical image data $D_2'$. When a plurality of times of simulated repair are performed changing the defect portion to be repaired, a plurality of the second pattern images $I_8$ estimated from the repaired optical image data $D_2'$ are obtained.

The second pattern images $I_7$ and $I_8$ are in the more advanced state than the first pattern images $I_5$ and $I_6$. For example, when the first pattern images $I_5$ and $I_6$ are exposure images of a circuit pattern transferred onto a wafer, the second pattern images $I_7$ and $I_8$ may be resist pattern images at any stage in a series of a lithography process such as development and etching or may be circuit pattern images finally formed in a wafer. The circuit pattern may be any of circuit patterns before and after the CMP processing.

A specific stage of the second pattern images $I_7$ and $I_8$ in the lithography process can be suitably selected according to the process.

For example, in the etching processing of a wiring material using a resist pattern as a mask, dimensional variation due to a microloading effect may occur. The dimensional variation increases as a density difference in a circuit pattern increases. This is because, between a region where a circuit pattern to be formed on a wafer is dense and a region where the circuit pattern is sparse, in the latter region a larger number of active species required for etching are inhibited. Consequently, the density of the circuit pattern required for a circuit pattern having a desired dimension (determined by pattern data as a basis) cannot be obtained. That is to say, in the region where a circuit pattern to be formed on the wafer is sparse, the dimension of the pattern formed by etching is larger than a desired pattern dimension. Meanwhile, in the region where the circuit pattern to be formed on the wafer is dense, the dimension of the pattern formed by etching is smaller than the desired pattern dimension.

To solve the above problem, correction processing for pattern data is performed over all minute sections in the circuit pattern. Consequently, although the pattern dimension after development processing deviates from a desired dimension, the pattern after etching has a desired dimension. Thus, in this example, if the second pattern image estimated by the second simulator 404 is a resist pattern image after development, all patterns may be possibly judged as defects. However, if the second pattern image is a resist pattern image after etching or a wiring pattern image, the presence of a defect can be accurately determined.

The second pattern images $I_7$ and $I_8$ estimated by the second simulator 404 are sent to the second comparing circuit 405. In the second comparing circuit 405, the second pattern image $I_7$ as a model and the second pattern image $I_8$ estimated from the optical image data $D_2'$ after simulated repair are compared with each other, whereby confirmation can be made as to whether or not the initially indicated defect on the wafer is eliminated. As the result of the comparison, the coordinate determined as a defect and the second pattern images $I_7$ and $I_8$ as the basis for the defect determination are output as a defect information list 209 to an external device along with the reference image data $D_1$ and the optical image data $D_2$.

As shown in FIG. 19, the defect information list 209 is sent to the review device 500. In the review device 500, an image at the defect portion of the mask is displayed while a table on which the mask is placed is moved so that the defect coordinates of defects can be observed one by one. At the same time, judgment of the defect determination, second pattern image $I_7$ and $I_8$, reference image data $D_1$ and optical image data $D_2$ as a basis for the determination, are arranged and displayed on a screen so that the judgment, the optical image and the reference image can be confirmed. The defect on the mask and the influence on the wafer transfer image are arranged and displayed in a review process, whereby the determination whether or not the mask pattern should be repaired is facilitated. In general, projection from the mask to the wafer is performed while reduction to approximately quarter size is performed, and therefore, when images are arranged and displayed, the reduction scale is considered.

All defects detected by the inspection system 100c are discriminated in the review device 500. However, when the defect detected in the wafer transfer image is minor, the defect may be removed from an object to be reviewed by pre-processing.

The discriminated defect information is returned to the inspection system 100c and stored in the storage unit 109. When even one defect to be repaired is confirmed in the review device 500, the mask is sent to a repair device 600, which is an external device of the inspection system 100c, along with a defect information list 210. Since the repair method is different according to the type of the defect, that is, between the extrusion and intrusion defects, the type of the defect including discrimination between the extrusion and intrusion defects and the coordinate of the defect are added to the defect information list 210.

In the fourth aspect of Embodiment 2, the inspection system 100c itself may have the review function. In this case, the mask inspection results 205 and the transfer image inspection results 206 are displayed as images with incidental information of the defect determination on the screen of the control computer 110 or a screen of a separately provided calculator. The image of the mask defect portion is displayed using an optical observation system image of the inspection system 100c.

The inspection system in the fourth aspect of Embodiment 2 is not limited to the above-mentioned example of FIG. 18 and may be repaired without departing from the spirit and scope of the present invention.

In this case, Unit A of the optical image data apparatus as shown in FIG. 18 can utilize an irradiating laser beam light source 103 However, optical image data can also be acquired using an electron beam. For example, the inspection apparatus can use SEM (Scanning Electron Microscope) or MEM (Mirror Electron Microscope).

Figure 24:
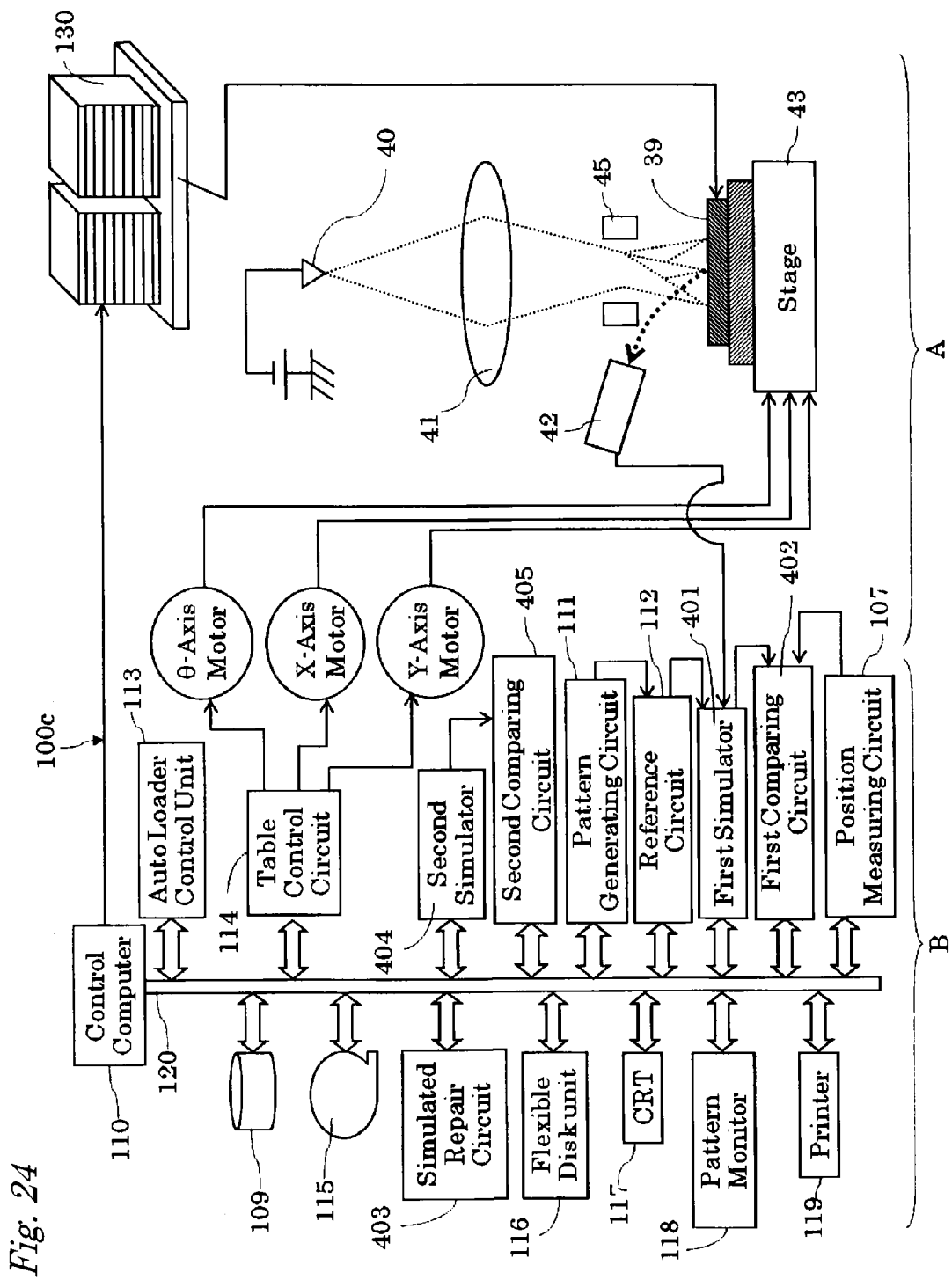
FIG. 24 is an example of optical image data acquisition using SEM (Scanning Electron Microscope) according to Embodiment 2.

The inspection apparatus as shown in FIG. 24 is an example of an inspection apparatus utilizing SEM technique. The individual component numbers are the same as for FIG. 18 with the exception of Unit A.

In FIG. 24 the electron beam from the electron gun 40 is focused by the condenser lens 41 and then irradiated to the mask 39 placed on the stage 43. The movement of the scanning line and scanning speed on the mask is controlled by the scanning coil 45. After the electron is irradiated on the mask the reflected electron beam is guided to the detector 42. The output signal from the detector is amplified by the sensor (not shown) then converted to digital data, this signal is then sent to the first simulator 401.

Figure 25:
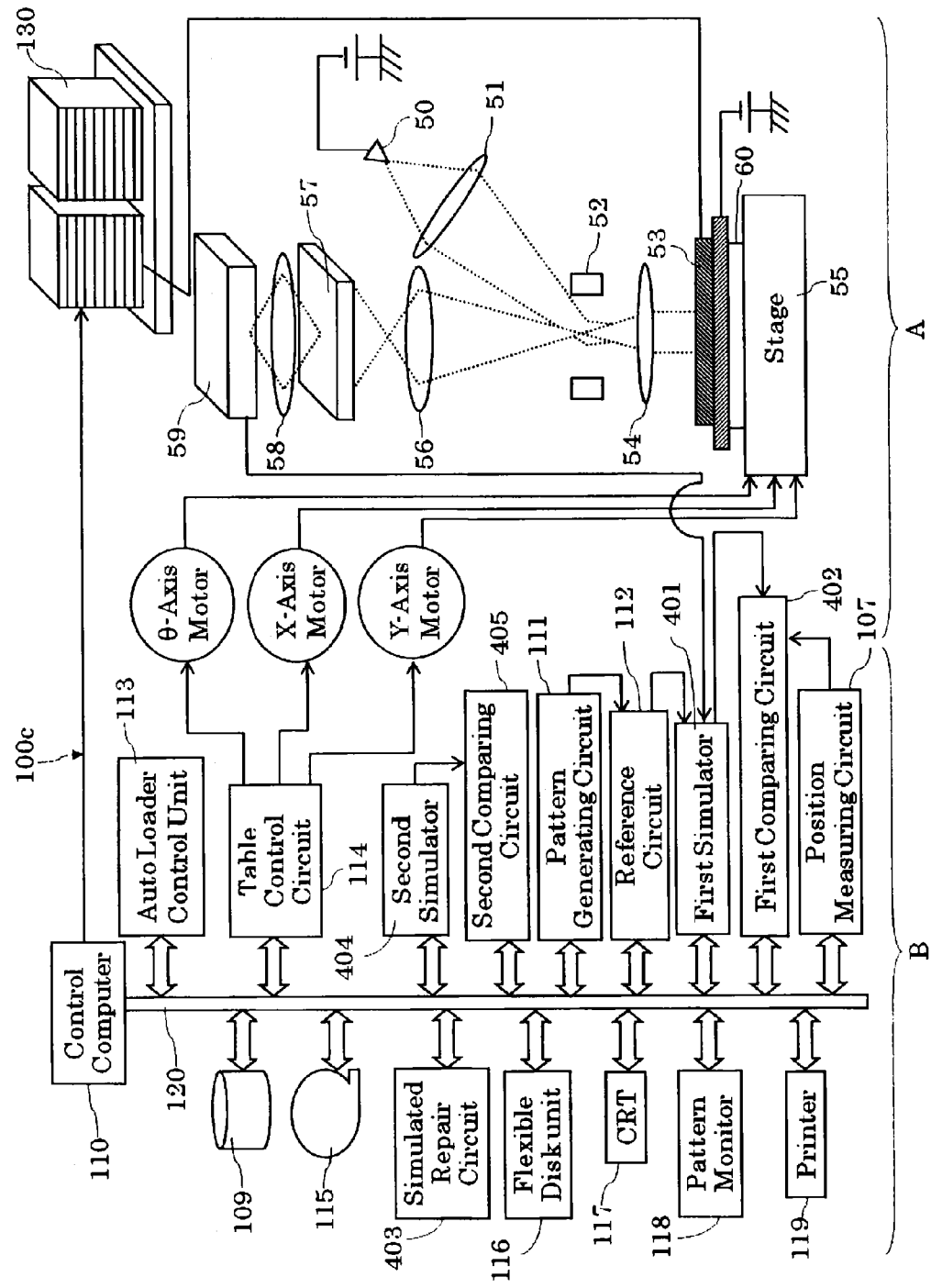
FIG. 25 is an example of optical image data acquisition using MEM (Mirror Electron Microscope) according to Embodiment 2.

FIG. 25 is another example using MEM to acquire optical Image data as in FIG. 18. The individual component numbers are the same as in FIG. 18 with the exception of Unit A.

In FIG. 25, the mask 53 is placed on an insulated material 60 on the stage 55. The electron beam from the electron beam gun 50 is focused by the condenser lens 51, then deflected by the ExB deflector 52, after, the electron beam passes through the objective lens 54 forming an expanded beam which reaches the mask 53 vertically. After the electron beam is irradiated on the mask 53 the reflected beam is transmitted through the objective lens 54 to the focus lens 56 and is then projected on to the fluorescent screen 57. The optical image on the fluorescent screen 57 is focused on the received light plate of CCD 59 by optical lens 58. Then, the image of pattern focused on the CCD 59 is transformed into digital data, which is sent to the first simulator 401.

As described above, in the inspection device according to the fourth aspect of the Embodiment 2, a pattern image after being transferred from the optical image to the wafer is estimated, and the pattern image is compared with the pattern image estimated from the reference image in a similar manner, whereby the presence of a defect is determined. After the simulated repair of the pattern image at the portion determined as a defect, the pattern image is compared with the image as a model again, and the presence of a defect is determined. Consequently, the defect on the mask, the influence of the defect on the wafer, and the degree of the improvement by the repair can be estimated. Thus, according to the inspection device and the inspection method of the present Embodiment, the level of the influence of the mask shape defect itself on the wafer and a portion of the pattern on the mask to be repaired for eliminating a detected defect can be indicated.

Further, the initial simulation is stopped at the previous stage of the lithography process relative to the later simulation, and therefore, in comparison with a case where simulation at the same stage as the later simulation is performed also in the previous simulation, the entire calculation processing associated with the defect estimation can be increased in speed.

FIG. 10 is a screen through which an operator browses the results of the defect determination based on the wafer transfer image and the resist image. The upper stage is a reference image or an optical image on the model side in the inspection using a die-to-die comparison method. The lower stage is an optical image on the test object side including the defect. In each stage, the images are (1) an image taken by a transmission optical system of the inspection device, (2) an image taken by a reflection optical system of the inspection device, (3) a mask image estimated from these images, (4) a wafer transfer image obtained by simulating and estimating exposure conditions based on the mask image, and (5) a resist image obtained by simulating and estimating characteristics of resist in sequence from the left of FIG. 10.

According to the review screen shown in FIG. 10, since the reference image, the optical image, and the transfer image estimated from them are arranged and displayed, the operator compares these images and can narrow down a defect to be reviewed.

FIG. 11 shows another example of the review screen in the inspection device. The screen is constituted of, for example, a window, through which the reference image as the basis for the defect determination and the optical image including the defect are displayed so that the operator can compare the reference image and the optical image, and a window through which the defect distribution in the inspection range on the mask is displayed. There may be further provided with a profile screen window through which a difference between the optical image and the reference image is displayed, the brightness of each pixel of the optical image and the reference image are dumped and displayed with numeric values, and the sensor brightness is displayed when sectioned by the x and y axes for the purpose of analyzing the defect.

The features and advantages of the Embodiment 2 may be summarized as follows.

According to the Embodiment 2, a defect estimation device is provided, which can estimate a defect on a mask, the influence of the defect on a substrate, and the degree of the improvement by repair.

According to the Embodiment 2, a defect estimation device is provided, which can estimate a defect on a mask, the influence of the defect on a substrate, and the degree of the improvement by repair and can increase the speed of the entire calculation process.

According to the Embodiment 2, a defect estimation method is provided, which can estimate a defect on a mask, the influence of the defect on a substrate, and the degree of the improvement by repair.

According to the Embodiment 2, an inspection device is provided, which can estimate a defect on a mask, the influence of the defect on a substrate, and the degree of the improvement by repair and therefore can indicate the level of the influence of the mask defect itself on a substrate and a portion of the pattern on the mask to be repaired for eliminating a detected defect.

According to the Embodiment 2, an inspection device is provided which can indicate the level of the influence of a mask defect itself on a substrate and a portion of the pattern on the mask to be repaired for eliminating a detected defect and can increase the speed of calculation processing associated with defect estimation.

The Embodiment 2 is not limited to the above-mentioned aspects and may be repaired without departing from the spirit and scope of the present invention.

In the above example, when a defect is estimated initially, simulation of an optical image obtained by transferring a pattern on a mask as a target by an exposure device is performed first. However, this invention is not limited to the example. For example, first, the reference image data $D_1$ of the mask as a target and the optical image data $D_2$ are compared. Candidates of a defect are estimated from the result of the comparison, and simulation may be performed. In this case, after the defect candidates are extracted, for the defect candidates, simulation of an optical image obtained by being transferred by an exposure device is performed, and if necessary, the subsequent simulation is performed. By doing this, defect candidates are further narrowed down, and thereafter, simulated repair may be performed. This can reduce the number of times of simulation requiring a long calculation time to one time.

The above description of the aspects of the Embodiment 2 has not specified apparatus constructions, control methods, etc. which are not essential to the description of the invention, since any suitable apparatus constructions, control methods, etc. can be employed to implement the invention. Further, the scope of this invention encompasses all estimation devices and methods, pattern inspection systems and pattern inspection methods employing the elements of the invention and variations thereof which can be designed by those skilled in the art.

What is claimed is:

1. An inspection device, which irradiates light to a sample formed with a pattern, forming an image of the sample on an image sensor through an optical system, and determines the presence of a defect, comprising:
   an optical image acquisition part which obtains an optical image of the sample from the image sensor;
   a first comparison part which compares the optical image with a reference image as a reference of the determination and, when a difference exceeds at least one of threshold values, determines that there is a defect;
   a transfer image estimation part which estimates by simulation an optical image obtained when each pattern of an optical image on the sample and the reference image is transferred by a transfer device; and a second comparison part which compares each of the transfer images and when a difference exceeds at least one of the threshold values, determines that there is a defect.

2. The inspection device according to claim 1, characterized by further comprising an output part, which outputs information from the first and second comparison parts to a review device or to a review screen for reviewing the information from the first and second comparison parts.

3. The inspection device according to claim 2, characterized in that the information from the first comparison part contains an optical image determined as defective and a coordinate of the defect, and the information from the second comparison part contains a transfer image of the optical image determined as defective and the coordinates of the defect.

4. An inspection method, which irradiates light to a sample formed with a pattern, forming an image of the sample on an image sensor through an optical system, and determines the presence of a defect, characterized by comprising:

obtaining an optical image of the sample from the image sensor;

comparing the optical image with a reference image as a reference of the determination and, when a difference exceeds at least one of threshold values, determining that there is a defect;

estimating a transfer image of the optical image and a transfer image of the reference image by simulation;

comparing the transfer image of the optical image and the transfer image of the reference image and when a difference exceeds at least one of the threshold values, determining that there is a defect; and reviewing the optical image, the reference image and each of the transfer images and determining necessity of repair to be applied to the defect.

5. The inspection method according to claim 4, characterized in that the transfer image of the optical image is estimated based on an optical image including all defects in a predetermined range.

6. The inspection method according to claim 4, characterized by further comprising:

obtaining an optical image, which is determined as a defect by comparing the optical image and the reference image, and simulating repair of the defect, wherein in the step of estimating the transfer image, a transfer image of the simulated optical image and a transfer image of the reference image are estimated.

7. The inspection method according to claim 6, characterized by further comprising, comparing each transfer image of the optical image and the simulated optical image and estimating a portion to be repaired when it is determined that the defect is required to be repaired.

8. An inspection device, which irradiates light to a sample formed with a pattern, forming an image of the sample on an image sensor through an optical system and determines the presence of a defect, characterized by comprising:

an optical image acquisition part which obtains an optical image of the sample from the image sensor;

a first comparison part which compares the optical image with a reference image as a reference of the determination and when a difference exceeds at least one of threshold values, determines that there is a defect;

a simulated repair part which obtains the optical image determined as defective by the first comparison part and simulates a repair to the defect;

a transfer image estimation part which estimates a transfer image of the optical image simulated by the simulated repair part and a transfer image of the reference image by simulation; and a second comparison part which compares each of the transfer images and when a difference exceeds at least one of the threshold values, determines that there is a defect.

9. The inspection device according to claim 8, characterized by further comprising an output part, which outputs information from the first and second comparison parts to a review device or to a review screen for reviewing the information from the first and second comparison parts.

10. The inspection device according to claim 9, characterized in that the information from the first comparison part includes an optical image determined as a defect and a coordinate of the defect and the information from the second comparison part includes a transfer image of the optical image determined as a defect and the coordinates of the defect.

* * * * *